US009892238B2

(12) United States Patent
Lahiri et al.

(10) Patent No.: US 9,892,238 B2
(45) Date of Patent: Feb. 13, 2018

(54) SYSTEM AND METHOD FOR MONITORING A PROCESS

(71) Applicant: Scientific Design Company, Inc., Little Ferry, NJ (US)

(72) Inventors: Sandip K. Lahiri, Hoora (BH); Mansoor Husain, North Brunswick, NJ (US)

(73) Assignee: SCIENTIFIC DESIGN COMPANY, INC., Little Ferry, NJ (US)

( * ) Notice: Subject to any disclaimer, the term of this patent is extended or adjusted under 35 U.S.C. 154(b) by 832 days.

(21) Appl. No.: 14/296,894

(22) Filed: Jun. 5, 2014

(65) Prior Publication Data

US 2014/0365195 A1  Dec. 11, 2014

Related U.S. Application Data

(60) Provisional application No. 61/832,450, filed on Jun. 7, 2013.

(51) Int. Cl.

| | |
|---|---|
| *G06F 19/00* | (2011.01) |
| *G06N 3/02* | (2006.01) |
| *G06N 3/08* | (2006.01) |
| *G05B 23/02* | (2006.01) |

(52) U.S. Cl.
CPC ......... *G06F 19/707* (2013.01); *G05B 23/024* (2013.01); *G05B 23/0254* (2013.01); *G06F 19/702* (2013.01); *G06N 3/02* (2013.01); *G06N 3/08* (2013.01); *G05B 23/0216* (2013.01); *G05B 2219/32201* (2013.01); *Y02P 90/22* (2015.11)

(58) Field of Classification Search
CPC .................................................... G06F 19/707
See application file for complete search history.

(56) References Cited

U.S. PATENT DOCUMENTS

| | | | |
|---|---|---|---|
| 5,859,964 A | 1/1999 | Wang et al. | |
| 2007/0151451 A1* | 7/2007 | Rekers | B01D 53/002 95/141 |
| 2008/0015814 A1* | 1/2008 | Harvey, Jr. | G05B 19/41875 702/179 |

(Continued)

FOREIGN PATENT DOCUMENTS

| | | |
|---|---|---|
| CN | 101438251 A | 5/2009 |
| CN | 101542407 A | 9/2009 |
| WO | 2006029290 A2 | 3/2006 |

OTHER PUBLICATIONS

Bulsari, Applications of artificial neural networks in process engineering, J. Syst. Engg. 1994, 4, pp. 131-170.

(Continued)

*Primary Examiner* — Manuel L Barbee
(74) *Attorney, Agent, or Firm* — Scully Scott Murphy and Presser; Frank Digiglio

(57) ABSTRACT

A system for monitoring a process determined by a set of process data in a multidimensional process data domain pertaining to process input-output data, the system comprising: means for acquiring a plurality of historic process data sets; means for obtaining a transformation from the multidimensional process data domain to a model data domain of lower dimension by performing multivariate data analysis; and means for transforming a current process data set to a model data set to monitor the process.

24 Claims, 16 Drawing Sheets

(56) References Cited

U.S. PATENT DOCUMENTS

2008/0082181 A1* 4/2008 Miller ................ G05B 23/021
                                                                                    700/30
2010/0036529 A1     2/2010    Landells et al.
2010/0161132 A1*  6/2010    Bharati ............. G05B 23/0254
                                                                                  700/266

OTHER PUBLICATIONS

Hecht-Nielsen, "Theory of the back propagation neural network", Proceedings of the international joint conference on neural networks, Washington D.C., Jun. 18-22, 1989, pp. 593-611, 1.

Huang et al., "Catalyst design for methane oxidative coupling by using artificial neural network and hybrid genetic algorithm", Chemical Engineering Science, accepted Aug. 30, 2002, pp. 81-87, 58.

Lahiri et al, "Development of an artificial neural network correlation for prediction of hold-up of slurry transport in pipelines", Chemical Engineering Science, available online Nov. 23, 2007, pp. 1497-1509, 63.

Lahiri et al, "Modeling of commercial ethylene oxide reactor: a hybrid approach by artificial neural network & differential evolution", International J. of Chemical reactor engineering, Jan. 2010, 28 pages, vol. 8, Article A4.

Riedmiller et al., "A direct adaptive method for faster backpropagation learning: the RPROP algorithm", Proc. of the IEEE Int. Conf. on Neural Networks, San Francisco CA, Mar. 28-Apr. 1, 1993, pp. 586-591.

Gill et al., "The Levenberg-Marquardt Method", §4.7.3 in Practical Optimization 1981, pp. 136-137, London: Academic Press.

Stephanopoulos et al., "Intelligent systems in process engineering: A review", Comp. & Chem. Engg., received for publication May 11, 1995, pp. 743-791, vol. 20, No. 6/7.

International search report dated Jun. 10, 2014 from related International Application PCT/IB2014/062010.

Chinese search report from Application 2014800432592.

\* cited by examiner

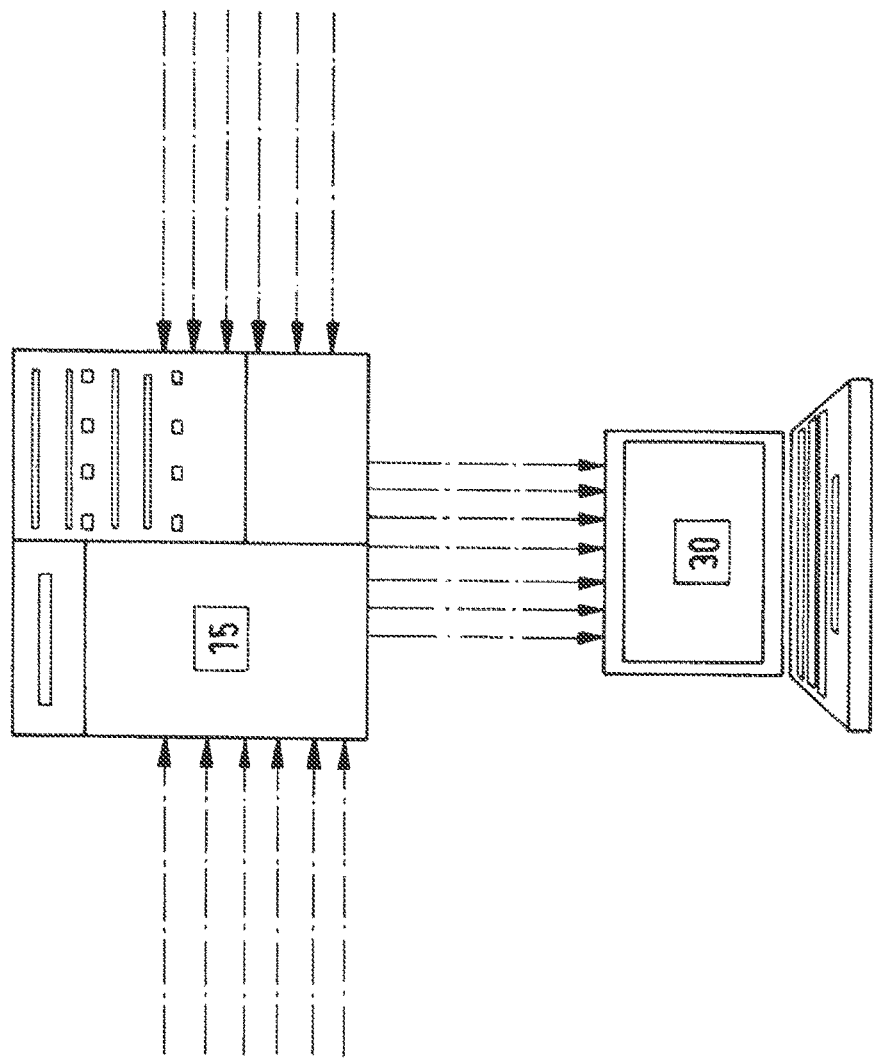

SYSTEM AND METHOD FOR MONITORING A PROCESS

CROSS REFERENCE TO RELATED APPLICATION

The present invention claims the benefit of U.S. Provisional Patent Application No. 61/832,450 filed Jun. 7, 2013, the entire content and disclosure of which is incorporated herein by reference.

FIELD OF INVENTION

The present invention relates to a system and method for monitoring a process. In particular, the present invention relates to a novel system and method of diagnosing an operating condition of the process.

BACKGROUND OF THE INVENTION

US 2010/0036529 pertains to a technique for detecting abnormal events in a process using multivariate statistical methods.

Early detection and diagnosis of an occurrence of an abnormal event in an operating plant is very important for ensuring plant safety and for maintaining product quality. Advancements in the area of advanced instrumentation have made it possible to measure hundreds of variables related to a process every few seconds. These measurements bring in useful signatures about the status of the plant operation.

A wide variety of techniques, for detecting faults, have been proposed in the literature. These techniques can be broadly classified into model-based methods and historical data based statistical methods. While model based methods can be used to detect and isolate signals indicating abnormal operation, for large scale complex chemical systems such quantitative or qualitative cause-effect models may be difficult to develop from the outset.

Artificial Neural Network (ANN)

Neural networks are computer algorithms inspired by the way information is processed in the nervous system.

Artificial Neural Networks (ANN) have emerged as a useful tool for non-linear modeling, especially in situations where developing phenomenological or conventional regression models becomes impractical or cumbersome. ANN is a computer modeling approach that learns from examples through iterations without requiring a prior knowledge of the relationships of process parameters. Consequently, ANN is capable of adapting to a changing environment. It is also capable of dealing with uncertainties, noisy data, and non-linear relationships.

ANN modeling methods have been known as 'effortless computation' and are readily used extensively due to their model-free approximation capabilities of complex decision-making processes.

The advantages of an ANN-based model are:

(i) it can be constructed solely from the historic process input-output data (example set), (ii) detailed knowledge of the process phenomenology is unnecessary for the model development, (iii) a properly trained model can be generalized easily due to its capability to accurately predict outputs for a new input data set, and (iv) even multiple input-multiple output (MIMO) non-linear relationships can be approximated simultaneously and easily.

Owing to their attractive characteristics, ANNs have been widely used in chemical engineering applications such as steady state and dynamic process modeling, process identification, yield maximization, non-linear control, and fault detection and diagnosis, see Lahiri, S. K. and Ghanta K. C, 2008, Lahiri, S. K. and Khalfe N, 2010, Tambe et. al. 1996, Bulsari 1994, Huang 2003 and Stephanopoulos and Han 1996, for instance.

The most widely utilized ANN paradigm is the multi-layered perceptron (MLP) that approximates non-linear relationships between an input set of data (independent process variables) and a corresponding output data set (dependent variables). A three-layered MLP with a single intermediate (hidden) layer accommodating a sufficiently large number of nodes, also termed neurons or processing elements, can approximate or map any non-linear computable function with high accuracy. An approximation is obtained or "taught" through a numerical procedure called "network training" wherein network parameters or weights are adjusted iteratively such that the network, in response to the input patterns in an example set, accurately reproduces the corresponding outputs.

There exists a number of algorithms—each possessing certain advantageous characteristics—to train an MLP network, for example, the most popular error-back-propagation (EBP), Quick propagation and Resilient Back-propagation (RPROP) (Reidmiller, 1993).

Training of an ANN involves minimizing a non-linear error function (e.g., root-mean squared-error, RMSE) that may possess several local minima. Thus, it may become necessary to employ a heuristic procedure involving multiple training runs in order to obtain an optimal ANN model whose parameters or weights correspond to the global or the deepest local minimum of the error function.

Network Architecture

A MLP network used in model development is depicted in FIG. 1: Architecture of feed forward neural network. As shown, the network usually consists of three layers of nodes. The layers described as input layer, hidden layer and output layers, comprise R, S and K number of processing nodes, respectively. Each node in the input layer is linked to all nodes in the hidden layer and each node in the hidden layer is linked to all nodes in the output layer using weighted connections. In addition to the R and S number of input and hidden nodes, the MLP architecture also provides a bias node (with fixed output of R+1, S+1, respectively) in its input and hidden layers, not shown. The bias nodes are also connected to all the nodes in the subsequent layer and provide additional adjustable parameters or weights for model fitting. The number of nodes R in the MLP network's input layer is equal to the number of inputs in the process whereas the number of output nodes K equals the number of process outputs. However, the number of hidden nodes S is an adjustable parameter whose magnitude may be determined by various factors, such as the desired approximation and generalization capabilities of the network model.

Network Training

Training a network consists of an iterative process in which the network is given the desired inputs along with the corresponding outputs for those inputs. It then seeks to alter its weights to try and produce the correct output (within a reasonable error margin). If it succeeds, it has learned the training set and is ready to perform upon previously unseen data. If it does not succeed to produce the correct output it re-reads the input and again tries to produce the corresponding output. The weights are slightly adjusted during each iteration through the training set known as a training cycle, until the appropriate weights have been established. Depending upon the complexity of the task to be learned, many thousands of training cycles may be needed for the network to correctly identify the training set. Once the output is correct the weights can be used with the same network on unseen data to assess how well it performs.

Back Propagation Algorithm (BPA)

In the back propagation algorithm network weights are modified to minimize the mean squared error between the desired output and the actual output of the network. Back propagation uses supervised learning in which the network is trained using data for which input data as well as desired output data are known. Once trained, the network weights are maintained or frozen and can be used to compute output values for new input samples. A feed forward process involves presenting input data to input layer neurons that pass the input values onto the first hidden layer. Each of the hidden layer nodes compute a weighted sum of input passes the sum through its activation function and presents the result to the output layer. The goal is to find a set of weights that minimize the mean squared error. A typical back propagation algorithm can be given as follows:

The MLP network is a non-linear mapping device that determines a K dimensional non-linear function vector f, where f: X→Y. Wherein, X is a set of N-dimensional input vectors (X={xp}; p=1, 2, . . . , P and x=[x1, x2, . . . , xn, . . . , xN]$^T$), and Y is the set of corresponding K-dimensional output vectors (Y={yp}; p=1, 2, . . . , P where y=[y1, y2, . . . , yk, . . . , yK]$^T$). The mapping f is determined by:

(i) network topology,
(ii) choice of an activation function used for computing outputs of the hidden and output nodes, and
(iii) network weight matrices $W^H$ and $W^O$ referring to the weights between input nodes and hidden nodes, and hidden nodes and output nodes, respectively. Thus, the non-linear mapping f can be expressed as (iv) $f: y = y(x; W)$     (1)

(v) where, $W = \{W^H, W^O\}$.

This equation suggests that y is a function of x, which is parameterized by W. It is now possible to write the closed-form expression of the input-output relationship approximated by the three-layered MLP as:

$$y_k = \tilde{f}_2\left[\sum_{l=0}^{L} w_{lk}^O \tilde{f}_1\left[\sum_{n=0}^{N} w_{nl}^H x_n\right]\right]; \quad k = 1, 2, \ldots K \quad (2)$$

Note that in equation 2, the bias node is indexed as the zeroth node in the respective layer.

In order for an MLP network to approximate the non-linear relationship existing between the process inputs and the outputs, it needs to be trained in a manner such that a pre specified error function is minimized. In essence, the MLP-training procedure aims at obtaining an optimal set W of the network weight matrices $W^H$ and $W^O$, which minimize an error function. The commonly employed error function is the average absolute relative error (AARE) defined as:

$$AARE = \frac{1}{N}\sum_{1}^{N}\left|\left(\frac{y_{predicted} - y_{experimental}}{y_{experimental}}\right)\right| \quad (3)$$

The most widely used formalism for the AARE minimization is the error-back propagation (EBP) algorithm utilizing a gradient-descent technique known as the generalized delta rule (GDR). In the EBP methodology, the weight matrix set, W, is initially randomized. Thereafter, an input vector from the training set is applied to the network's input nodes and the outputs of the hidden nodes and output nodes are computed.

The outputs are computed as follows. First the weighted-sum of all the node-specific inputs is evaluated, which is then transformed using a non-linear activation function, such as the logistic sigmoid function. The outputs from the output nodes are then compared with their target values and the difference is used to compute the AARE defined in equation. 3. Once the AARE is composed, the weight matrices $W^H$ and $W^O$ are updated using the GDR framework. Repeated with the remaining input patterns in the training set the procedure completes one network training iteration. For the AARE minimization, several training iterations may usually be necessary.

Generalizability

Neural learning is considered successful only if the system can perform well on test data on which the system has not been trained. This capability of a network is called generalizability. Given a large network, it is possible that repeated training iterations successively improve the performance of the network on training data e.g., by "memorizing" training samples, but the resulting network may perform poorly on test data i.e., unseen data. This phenomenon is called "overtraining". A proposed solution is to constantly monitor the performance of the network on the test data.

Hecht-Nielsen (1990) proposes that the weight should be adjusted only on the basis of the training set, but the error should be monitored on the test set. Here we apply the same strategy: training continues as long as the error on the test set continues to decrease and is terminated if the error on the test set increases. Training may thus be halted even if the network performance on the training set continues to improve.

Principal Component Analysis (PCA)

Often it is time consuming to monitor a plant condition in modern complex process industries as there is abundance of instrumentation that measure thousands of process variables in every few seconds. This has caused a "data overload" and due to the lack of appropriate analyses very little is currently being done to utilize this wealth of information. Given the current process control computer systems (DCS, on-stream analyzers and automated quality control labs) in modern chemical plants, it is not uncommon to measure hundreds of process variables online every few seconds or minutes, and tens of product variables every few minutes or hours.

Although a large number of variables may be measured, they are almost never independent; rather, they are usually very highly correlated. The true dimension of the space in which the process moves is almost always much lower than the number of measurements. Fortunately in data sets with many variables, groups of variables often move together because more than one variable may be measuring the same driving principle governing the system behavior. In many petrochemical systems there are only a few such driving forces. But an abundance of instrumentation allows us to measure dozens of system variables.

When this happens, one can take advantage of this information redundancy. For example, one can simplify the problem by replacing a group of variables with a single new variable. PCA is a quantitatively rigorous method for achieving this simplification. Multivariate statistical methods such as PCA (Principal Component Analysis) are capable of compressing the information down into low dimensional spaces which retain most of the information. The method generates a new set of variables, called principal components. Each principal component is a linear combination of the original variables. All the principal components are orthogonal to each other so there is little or no redundant information.

Principal component analysis comprises extracting a set of orthogonal, independent axes or principal components that are linear combinations of the variables of a data set, and which are extracted or calculated such that the maximum extent of variance within the data is encompassed by as few principal components as possible. The first principal component is calculated to account for the greatest variance in the data; the second principal component is then calculated to account for the greatest variance in the data orthogonal to the first principal component, the third to account for the greatest variance in the data orthogonal to the first two principal components, and so on. For each principal component extracted, less and less variance is accounted for. Eventually, the extraction of further principal components no longer accounts for significant additional variance within the data. By such means, a multi-dimensional or multi-variable data set can be reduced to fewer dimensions or principal components, while still retaining as much useful information within the resulting data as possible, which greatly simplifies analysis of the process data.

The position of a data point along a given principal component is referred to as its "score". The weighting of a variable for a given principal component is referred to as its "loading".

SUMMARY OF THE INVENTION

It is an object of the present invention to provide means for monitoring a process using real time process data, and to detect abnormal behavior of the process based on the monitoring in the presence of fluctuations in the process data over time.

According to an aspect of the present invention, a system for monitoring a process determined by a set of process data in a multi-dimensional process data domain pertaining to process input-output data, the system includes means for acquiring a plurality of historic process data sets; means for obtaining a transformation from the multidimensional process data domain to a model data domain of lower dimension by performing multivariate data analysis; and means for transforming a current process data set to a model data set to monitor the process.

According to an aspect of the present invention, a computer program product comprising a non-transitory computer-readable medium embodying program instructions causes a system to perform the steps of: acquiring a plurality of historic process data sets; obtaining a transformation from the multidimensional process data domain to a model data domain of lower dimension by performing multivariate data analysis; and transforming a current process data set to a model data set to monitor the process.

BRIEF DESCRIPTION OF THE DRAWINGS

FIG. 4 shows a data historian server connected to a dedicated PC loaded with PCA and ANN software.

FIG. 5a shows PCA scores plotted against principal component axes PC1 and PC2, respectively.

DETAILED DESCRIPTION OF THE INVENTION

Example of a Process to be Monitored

Oxidation of ethylene to produce ethylene oxide or EO is an important reaction in the petrochemical industry for synthesis of glycol, for instance. Commercially EO is produced in shell and tube type EO reactors by reacting oxygen and ethylene at high temperature and pressure in presence of silver based catalyst. The oxidation of ethylene involves a main reaction producing EO and an undesirable side reaction producing carbon dioxide or $CO_2$.

Desired Main Reaction
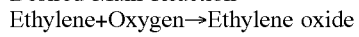
Ethylene+Oxygen→Ethylene oxide
Undesired Side Reaction
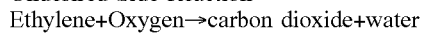
Ethylene+Oxygen→carbon dioxide+water The performance of the reaction is measured by selectivity which is calculated by the percentage of ethylene used to produce EO as compared to total ethylene used to produce EO and $CO_2$. Indirectly, selectivity measures the extent of the first reaction as compared to the second reaction. Selectivity has a profound effect of the efficiency and hence the overall economics of the glycol plant.

An EO reactor may be built like a shell and tube heat exchanger. Silver catalyst may be put as a fixed bed in a tube side. Water is circulated through the shell side to remove the heat of reaction as both the reactions are exothermic. The conversion of ethylene to EO is very low, therefore ethylene and oxygen are recycled back as illustrated in FIG. 3.

Figure 3:
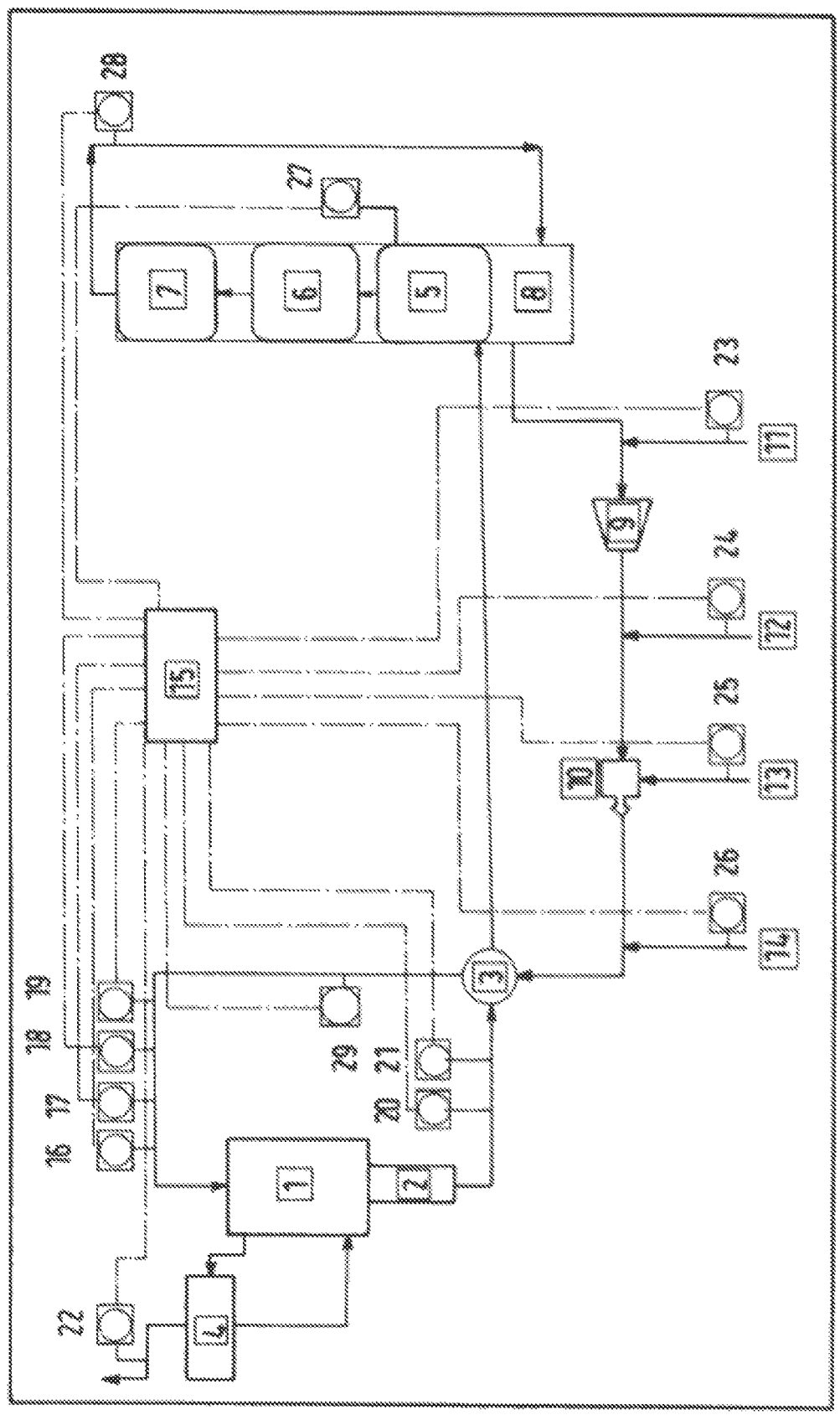
FIG. 3 shows an example of an ethylene oxide reactor.

FIG. 3: Schematic of EO reactor and associated unit shows a typical ethylene oxide reactor along with downstream ethylene oxide scrubber, carbon dioxide contactor and wash section. A mixture of gas, namely cycle gas is fed to the ethylene oxide reactor (1) from top and continuously pure oxygen (13), ethylene (14) and methane (11) is fed to the cycle gas system as shown in FIG. 3. The reactor may be built like a shell and tube heat exchanger wherein high selectivity catalyst pellets may be loaded as packed bed at the tube sides. Coolant is circulated through the shell side to remove heat of reaction and thus produce steam in steam drum (4). Ethylene and oxygen are partially reacted in the catalyst bed producing ethylene oxide (EO), carbon dioxide and water. Reactor outlet gas is further cooled in gas cooler (2) and gas-gas exchanger (3) and fed to the ethylene oxide scrubber (5) to absorb EO by water. Cycle gas from the EO scrubber top is fed to the $CO_2$ contactor (6) to absorb carbon dioxide by carbonate solution and finally to wash section (7) to wash any residual carbonate particles. Cycle gas from the top of the wash section is fed to knock out drum (8) to remove any liquid and finally recycled back to the EO reactor via cycle gas compressor (9). A chloride activator (14), preferably ethylene dichloride EDC or ethyl chloride EC is continuously fed to the cycle gas in a small quantity which acts as an activator and selectivity promoter in EO reaction system. A small amount of chloride (in ppm level) coming from activator is sufficient to increase the selectivity and activity of catalyst. EDC or EC inhibits the combustion reaction, i.e., the second reaction to a greater extent than the epoxydation reaction, i.e., the first reaction. In this way, EDC or EC promotes the selectivity for EO. Less than optimum quantity of inhibitor reduces selectivity and produces more carbon dioxide. Thus the optimum value of inhibitor concentration at reactor inlet is crucial for maximizing EO production. Over-dosing and under-dosing of activator can reduce the catalyst selectivity drastically and lead to abnormal situation. Optimum dosing of activator is thus necessary for maintaining highest selectivity all the time. However, optimum dosing rate is not constant and can vary with catalyst age, chloride losses from the system and reactor temperatures, for instance.

Because of the complex dynamics of the process, it is very difficult to calculate the optimum chloride dosing rate theoretically. High selectivity catalyst is very sensitive to the chloride dosing rate and any deviation from the optimum dosing rate has an adverse effect on selectivity and overall economics of the process.

Typically, there may be in the region of 20 independent and 35 dependent variables associated with such a process, not all of which are shown in this example. Independent variables measured include the cycle gas inlet composition nine components, such as oxygen, ethylene, methane, ethane, carbon-dioxide, water, ethylene oxide, nitrogen and argon measured by online analyzer (17), cycle gas flow (16), pressure (19), coolant temperature (18), chloride concentration at reactor inlet gas (i.e., different chloride species such as ethylene di-chloride, ethyl chloride, vinyl chloride, methyl chloride, allyl chloride measured by online chloride analyzer (29)), methane flow (23), ethylene flow (24), oxygen flow (25), EDC flow (26), EO scrubber top temperature (27), wash tower top temperature (28) etc. Examples of dependent variables include cycle gas outlet composition (9 components as specified above measured by analyzer (20)), selectivity of catalyst (21), EOE production (calculated), steam generation in steam drum (22) etc. All the sensors and meters are interfaced to an online real time data historian (15) as shown in FIG. 3.

Acquiring Historic Process Data Sets to Build an ANN Model

Collection of Data

The quality and quantity of data is important in ANN modeling as neural learning is primarily based on these data. In an example of monitoring a process an hourly average of actual plant operating data was collected at steady state for approximately six months. Normally, in modern glycol plants all the real time process data are continuously send to a Control Computer System or DCS console from various sensors and transmitters. Also, a plant DCS may be adapted to collect and save the all real time data in a plant historian (e.g., PI system, IP21 or Exaquantum, to name a few examples of a commercially available data historian) so that these data may be retrieved at a later date with a time stamp on it. These data historians are adapted to download all the process data in a spreadsheet for any historic date and time. This feature may be utilized to collect steady state data of the plant.

In the example, data was checked and cleaned from obvious inaccuracy and retains those data representative of plant operation in steady state and smooth. Finally, approximately 4000 records are qualified for neural modeling. The range of data collected includes plant operation data at various capacities starting from 80% capacity to 110% of design capacity i.e., the capacity of the plant as designed. Also these data comprise data collected during plant operations at different age of catalyst life.

Criteria of Selection of Input and Output Parameters

In order to choose the appropriate input and output parameters for the neural modeling the following observations are made. An exemplary neural model may serve at least the following purposes:

Monitor reactor conditions and diagnose any abnormality quickly.

Ensure chloride addition rate is optimum and maximize selectivity.

Monitor catalyst selectivity and activity.

Based on the above criteria, according to one embodiment, the output parameters are chosen to monitor reactor performance and comprise or consist of one or more of the group of: oxygen conversion, catalyst feed selectivity (feed selectivity) and reactor coolant temperature as shown in table 1. These output parameters may vary depending upon plant configurations. Additional parameters may be chosen according to one aspect of the invention. According to one embodiment of the invention, the output parameters comprise or consist of the above output parameters as also given in Table 1.

TABLE 1 input and output parameters of ANN based EO reactor model

| Input parameters | Unit |
|---|---|
| Inlet Oxygen concentration | mol % |
| Inlet Ethylene concentration | mol % |
| Inlet carbon-di-oxide concentration | mol % |
| Gas hourly space velocity | $hr^{-1}$ |
| Delta EO | mol % |
| Work rate | kg/hr/m3 |
| Cumulative EO production/m3 of catalyst | MT/m3 |
| Total chloride concentration | ppm |
| EO scrubber top temperature | ° C. |
| wash tower top temperature | ° C. |
| Output parameters | |
| Oxygen conversion | mol % |
| Feed selectivity | mol % |
| Reactor coolant temperature | ° C. |

Output parameters are chosen based on operating experience of the EO reaction section and pilot plant research experience. These three parameters may be indicative of the efficiency of EO reaction. The first parameter, oxygen conversion, represents the amount of reaction (both desirable and undesirable) that occurs in an EO reactor and thus indirectly represents how extensively the catalyst is used. The second parameter, feed selectivity, represents the efficiency of catalyst i.e., how efficiently the catalyst promotes the desirable reaction over undesirable ones. The third parameter, reactor coolant temperature, i.e., reactor temperature, represents the catalyst activity. Higher temperature means that the catalyst is less active and vice versa for a given EO production rate.

Based on operating experience in a glycol plant, all physical parameters that influence oxygen conversion, feed selectivity and reactor temperature are put in a so-called 'wish-list' for further consideration.

Out of the number of entries in the 'wish list', extensive pilot plant studies and micro reactor tests were carried out to shortlist the input parameters which can affect the model output parameters as described above.

Subsequently, ANN regression may be used to establish the best set of chosen inputs, which describes reaction behavior. The following criteria guide the choice of the set of inputs:

The number of inputs should be as low as possible.

Each input should be highly cross-correlated to the output parameter.

The inputs should be weakly cross-correlated to each other.

The selected input set should give the best output prediction, which is checked by using statistical analysis, e.g., average absolute relative error (AARE), standard deviation, cross-correlation coefficient.

There should be low complexity in neural network architecture, i.e., a low number of hidden layers.

The criteria mentioned above were then used to identify the most pertinent set of input parameters. Based on the above analysis, ten input parameters have been identified to predict the output parameters oxygen conversion, feed selectivity and reactor temperature, as shown in table 1. According to one embodiment of the invention, the input parameters comprise or consist of one or more of the group of: reactor $O_2$ inlet concentration (inlet oxygen concentration), $C_2H_4$ inlet concentration (inlet ethylene concentration), $CO_2$ inlet concentration (inlet carbon dioxide concentration), gas hourly space velocity, delta EO (across reactor), work rate, cumulative EO production (per $m^3$ of catalyst), total chloride concentration, scrubber top temperature (EO scrubber top temperature) and wash tower top temperature as also shown in Table 1. These input parameters may vary depending upon plant configurations. Additional parameters may be chosen according to one aspect of the invention.

According to one embodiment of the invention, the input parameters comprise or consist of the above input parameters as also given in Table 1.

Building an ANN Based EO Reactor Model

Complexity of EO Reactor Modeling

As to date there is no primary model found in the prior art which can accurately predict the output of an industrial EO reactor. Especially research on chloride interaction effect on the EO reaction in industrial situations is very limited.

Therefore it is desirable to build a reliable primary model for an industrial EO reactor which takes the following complexities into account:

EO reactor model is highly non-linear catalyst selectivity and activity is changing with the age of the catalyst.

The sensitivity of reaction input parameters (like chloride concentration, oxygen, ethylene concentration, etc.) towards catalyst selectivity and catalyst activity may change with time. This change is more pronounced in high selectivity and medium selectivity catalysts. For example, one unit of chloride change will change the catalyst selectivity differently at a different age of the catalyst life.

The model equations and/or model co-efficients may change as the catalyst characteristic changes.

Any static model, like the DMC model, build for one time data, may not be valid or successful for the whole catalyst life. It needs to be rebuilt or retrained periodically.

Model Building

With reference to table 1 for modeling purposes, the reaction operating conditions input parameters can be viewed as an example input matrix X of size (4000*10), and the corresponding reaction operating conditions output data as an example output matrix (Y) of size (4000*3). For ANN training, each row of X represents a ten-dimensional input vector x=[x1, x2, . . . , x10], and the corresponding row of matrix Y denotes the three-dimensional desired or target output vector y=[y1, y2, y3]. As the magnitudes of input and output differ greatly from each other, they are normalized in 0-1 scales. To avoid 'over training' phenomena described above, 80% of the total dataset was chosen randomly for training and the remaining 20% of the total dataset was selected in view of validation and testing.

In an example, ten parameters were identified as input parameters for ANN and the oxygen conversion, feed selectivity and reactor temperature designated as output parameters or as the target. These data were then used to build an ANN model as described above.

An advantage of the ANN based modeling is that a comprehensive multiinput-multioutput (MIMO) model can be constructed for all the process outputs namely oxygen conversion (y1), catalyst selectivity (y2) and reactor temperature (y3).

While the training set was used in the example for the EBP based iterative updating of the network weights, the same test set was used for simultaneously monitoring generalization of the MLP model. The MLP architecture comprised ten input (N=10) and three output (K=3) nodes.

In an example for developing an optimal MLP model, its structural parameter, namely the number of hidden nodes (L), activation functions in the input layer and the output layer, the learning rate and ANN algorithm was varied systematically. For choosing an overall optimal network model, the model with lowest AARE was selected for the test set (see below).

Assessment of Performance of ANN Model

There are different measures by which ANN performance is assessed, with validation and leave-one-out error estimates being the most commonly used one can divide the total available data as training data (80% of data) and test data (20% of the data chosen randomly). The ANN algorithm was trained on training data but the ANN performance is estimated on test data.

Statistical analysis of ANN prediction may be based on the following performance criteria:

1. The average absolute relative error (AARE) on test data should be minimum $$AARE = \frac{1}{N}\sum_{1}^{N}\left|\left(\frac{y_{predicted} - y_{experimental}}{y_{experimental}}\right)\right|$$

2. The standard deviation of error(s) on test data should be minimum $$\sigma = \sqrt{\frac{1}{N-1}\sum_{1}^{N}[|(y_{pred,i} - y_{exp,i})/y_{exp,i}| - A]^2}$$

3. The cross-correlation co-efficient (R) between input and output should be approximately equal to unity.

$$R = \frac{\sum_{i=1}^{N} (y_{exp,i} - \overline{y}_{exp})(y_{pred,i} - \overline{y}_{pred})}{\sqrt{\sum_{i=1}^{N} (y_{exp,i} - \overline{y}_{exp})^2} \sqrt{\sum_{i=1}^{N} (y_{pred,i} - \overline{y}_{pred})^2}}$$

ANN learning is considered successful if the system can perform well on test data on which the system has not been trained.

After optimization of ANN model tuning parameters, the model output obtained was summarized in table 2. Out of all the possibilities, Marquard Levenburg algorithm (Gill, 1981) with ten number of nodes in hidden layer and tan hyperbolic and linear function in input layer and output layer has been chosen as preferable solution (with lowest AARE) for the present case. The low AARE for oxygen conversion, selectivity and reactor temperature are 0.4, 0.05 and 0.48%, respectively, and may be considered as an excellent prediction performance considering the poor understanding of EO reaction phenomena and the large database for training comprising various production capacities and different catalyst ages.

TABLE 2

Prediction error by ANN based EO reactor model

| Performance criteria | Oxygen conversion | Feed selectivity | Reactor coolant temperature |
|---|---|---|---|
| Training set | | | |
| AARE | 0.004 | 0.0005 | 0.0048 |
| Sigma | 0.0057 | 0.0005 | 0.0057 |
| R | 0.999 | 0.999 | 0.999 |
| Test set | | | |
| AARE | 0.0041 | 0.0006 | 0.0077 |
| Sigma | 0.0058 | 0.0006 | 0.0067 |
| R | 0.998 | 0.998 | 0.998 |
| Optimum number of nodes | 10 | | |
| Input activation function | Tan hyperbolic | | |
| Output activation function | Linear | | |
| Optimum learning rate | 0.042 | | |
| Best training algorithm | Marquard Levenburg | | |

Using ANN Model for Fault Detection

Once an offline ANN model is developed, it can be used to predict real time output based on real time input of plant. The model predicted output is then compared with the actual output. Since during training phase, the error % between actual output and model predicted output was very less, online ANN model is also expected to generate very less error % (usually less than 1%) during normal operation. But if any abnormal event occurred in the process, this prediction error % will rise very sharply and thus generate a fault signal. In this way, ANN model can be used to detect fault in the process in real time.

Figure 1:
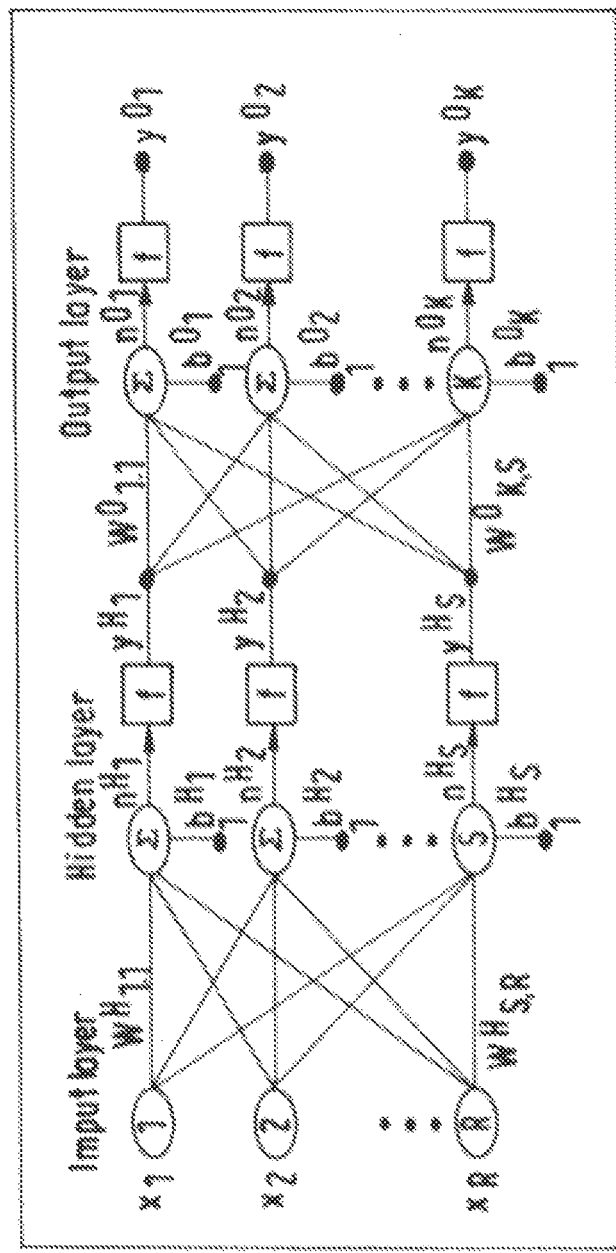
FIG. 1 shows the architecture of a feed forward artificial neural network.
Figure 2:
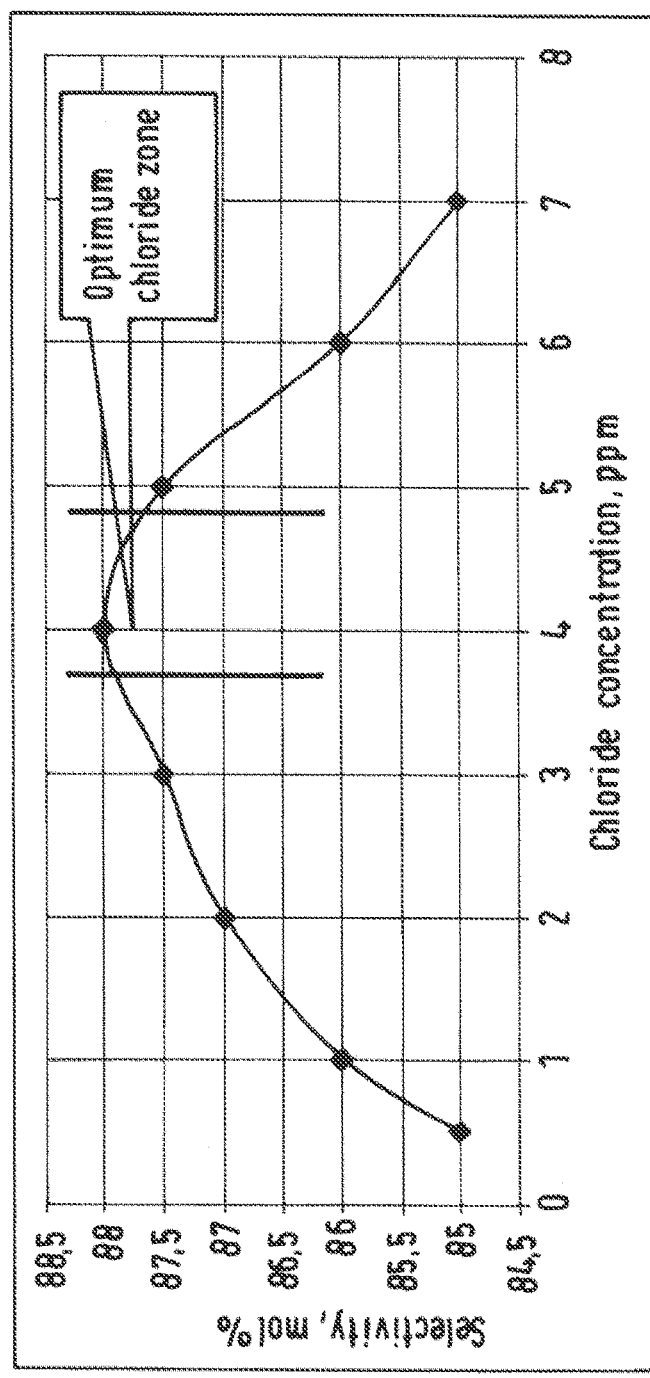
FIG. 2 shows a graph depicting catalyst selectivity as a function of chloride concentration.

Once a satisfactory ANN EO reactor model referred to as offline model, has been built this model can then be used in an online real time system. In an online real time system, real time ANN input data is fed from the data historian to a computer where ANN software is loaded, see FIG. 2. FIG. 2 shows a graph depicting selectivity vs. chloride concentration for high and medium selectivity catalysts. The ANN model may immediately calculate 3 ANN output parameters and error percentages immediately with the help of ANN model.

Figure 9:
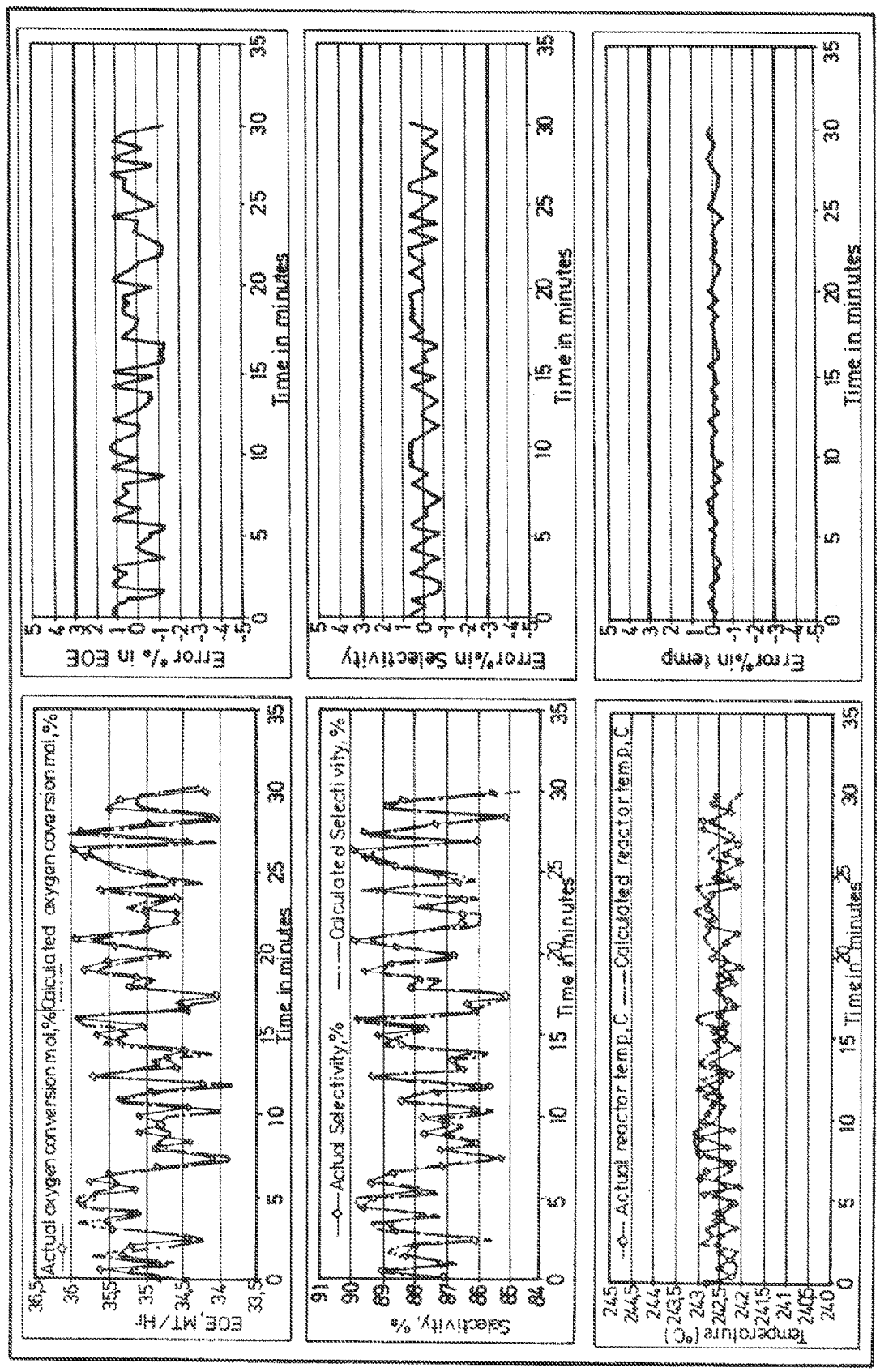
FIG. 9 shows graphs of actual process output together with ANN model predicted output over time.

Actual output along with predicted output parameter values are plotted in real time basis as shown in FIG. 9. FIG. 9: ANN prediction performance in real time, shows the goodness of the ANN model prediction with actual plant data. As long as prediction error percentages of the 3 outputs are within a threshold the (in this case 3%) process is considered as normal. If at any point of time, the prediction error percentages increase beyond their maximum limit, a fault signal is generated and it is concluded that an abnormal event has occurred.

Abnormal Events Observed in EO Reaction Systems

Possible in an EO reaction system abnormal events are taken from past experience of 20 years of various EO/EG plant worldwide. Some, but not all, of the major abnormal events in EO reaction systems may include:

Catalyst is overchlorided and catalyst selectivity subsequently lost.

Catalyst is underchlorided and selectivity is lost.

Loss of catalyst activity.

Sudden increase of total chloride at reactor inlet gas due to increased chloride feed or decrease in chloride losses from the system.

High EO breakthrough from ethylene oxide scrubber overhead which has an adverse effect on catalyst selectivity and activity.

High moisture carryover from wash tower top which has a negative effect on catalyst selectivity.

High $CO_2$ concentration at reactor inlet gas due to problem in $CO_2$ removal unit.

Formation of hot spots or any burning reaction inside the reactor tubes.

Sudden increase or decrease of reactor capacity.

Any other abnormal event including, but not limited to, any flow transmitter malfunction in the reactor loop, chloride analyzer or mass spectrometer (or gas chromatograph) malfunction etc.

Criteria of Selection of Input Parameters for PCA

To build a reliable PCA model it is crucial to choose appropriate input parameters. The input parameters may be chosen such that all the potential abnormal events in EO reaction system may be captured.

For high selectivity and medium selectivity catalysts it is very important to operate the chloride level in optimum chloride zone, see FIG. 2. This optimum zone is very narrow, as shown in FIG. 2 and any deviation of chloride outside this zone will cause the selectivity to drop drastically.

Normally, the catalyst is expected to run or operate at the optimum zone in plant. Any deviation of catalyst operation from the optimum zone is hard to detect by panel operators and selectivity will drop sharply if it remains undetected. Input parameters are chosen to capture quickly the under chloride and over chloride zone.

Following observations may be used to select the input parameters for PCA model building:

Use process knowledge and plant operating experience to shortlist symptom and root cause parameters:

Initially, abnormal events are chosen one by one for further study. As an example, the first abnormal event listed above is chosen, namely "Catalyst is overchlorided and catalyst selectivity subsequently lost" for further analysis. Plant operating experience, domain knowledge of EO reaction system is now applied to identify all the related input parameters which can capture the occurrence of the abnormal event. Some parameters are identified which can be considered as symptomatic of the abnormal event. Some other parameters are identified which are root cause of the abnormal event. Logical reasoning is done to understand what might happen during overchlorided of catalyst. Based on experience and process knowledge, all the symptoms and root cause parameters are identified. As for example, selectivity will drop sharply and outlet oxygen concentration will also drop during overchlorided event. So these two parameters can be chosen as symptom parameters. EDC flow increase and subsequent total chloride increase is considered as root cause parameters for overchlorided phenomena. Root cause parameters are not always so obvious. Like the example, EDC flow may not increase but the chloride losses from the system may reduce and thus increase the total chloride at reactor inlet. There is no direct indication of chloride losses from the system, so indirect parameters like scrubber top temperature, wash tower top temperature can be included also as root cause parameters.

Use actual operating data to add more parameters: In a lifetime of a plant, these types of abnormal events happened occasionally. When these type of abnormal even happened in plant, operating people usually write details about the occurrence in their daily log books. These log books and plant historic process data were studied to identify the time period when these abnormal events occurred actually in plant in past. All the related parameters during this time period are investigated in detail to identify more symptoms and root cause parameters. Statistical methods may be used to find correlation coefficients between catalyst selectivity and other parameters. Parameters having correlation coefficient between 0.5-1 (highly positively correlated) and −0.5 to −1 (highly negatively correlated) are observed more closely and included as input of PCA.

Study the parameters which change fast during abnormal event: There are some parameters which change very fast when abnormal events happened (may be within few minutes after the occurrence of any abnormal events) in contrast to some parameters which change very slowly (may be after several hours).

As for example for overchlorided phenomena, outlet oxygen concentration changes very fast (say within few minutes) in contrast to change in selectivity (which takes 4-6 hrs to respond). Fast changing parameters were given more priority over slow changing parameters so that any abnormality in the process can be detected quickly. The trend of each and every parameter shortlisted in step 2 above is studied in detail and fast changing parameters are given priority in the short listing. Expert knowledge of choosing the input parameters is necessary to capture the change in the system quickly during an abnormal event.

Number of input parameters should be minimum: Number of input parameters should be as small as possible to detect all features of an abnormal event as listed above. A most simple fault diagnosis PCA model will avoid unnecessary fault detection due to noise or malfunction of large number of transmitters for input parameters. Also redundant process parameters are avoided. As for example the reactor steam drum pressure and reactor coolant temperature are related by steam table relations and thus represent redundant information. So any one of them is sufficient to include as input parameters.

Table 3 gives a list of input parameters chosen for PCA model building in an exemplary EO/EG plant.

TABLE 3 input parameters of PCA based EO reactor model

| Input parameters | Unit |
| --- | --- |
| Inlet Oxygen concentration | mol % |
| Outlet Oxygen concentration | mol % |
| Inlet Ethylene concentration | mol % |
| Outlet Ethylene concentration | mol % |
| Cycle gas purge flow | MT/hr |
| Inlet carbon-di-oxide concentration | mol % |
| Inlet ethane concentration | mol % |
| Cycle gas flow | MT/hr |
| Delta EO | mol % |
| EOE production | MT/hr |
| Reactor inlet gas temperature | ° C. |
| Reactor coolant temperature | ° C. |
| Gas cooler outlet gas temperature | ° C. |
| Total chloride concentration | ppm |
| EO scrubber top temperature | ° C. |
| wash tower top temperature | ° C. |
| DI unit flow | MT/hr |
| Steam production from reactor | MT/hr |
| Feed selectivity | mol % |
| Cycle gas pressure | Kg/cm2 |

How PCA Input Data are Captured in Real Time:

The quality and quantity of data is crucial in PCA modeling as the final model is primarily based on these data. In an example actual plant operating data with every 2 minute at steady state was collected for approximately for six months. As stated earlier, a plant data historian (e.g., PI system, IP21 or Exaquantum, to name a few for commercial available data historian systems) is used to collect all the historical data.

There are two types of data in PCA. The first type of data is called normal plant data, which are data when the plant running normally and smoothly.

The evidence and time span of a smooth running plant can be found by careful reading of daily logs maintained by operating personnel in the control room. The second type of data is data of input parameters when any abnormal event happens in the plant. Again the timing and nature of abnormal event is retrieved from the daily log book. These data are kept in a separate file with an indication of the corresponding abnormal event.

How do PCA Input Data Relate to ANN Input/Output Data?

PCA input data are not same as ANN input/output data though some parameters are common because the way they detect and/or diagnose a fault is different. The objective of PCA and ANN are different though they both monitor the similar processes for any abnormality. By application of PCA, a multi-dimensional or multi-variable data set can be reduced to fewer dimensions, i.e., the principal components while still retaining as much useful information within the data as possible, which greatly simplifies analysis of the process data, and the detection of any abnormal events. ANN on the other hand used a reactor model to predict the key performance parameters of catalyst based on information received from its input parameters. ANN models are trained with steady state hourly average data when plant is running normal and smooth. As long as the ANN model can predict performance parameters with accuracy, it indicates that operation is steady and normal. When the actual performance parameters differ significantly from ANN prediction, it indicates that something abnormal happened in the process so that the process is no longer behaving as per its trained model.

The following table shows some key difference between PCA input parameters and ANN parameters.

TABLE 4

Difference between PCA input data and ANN input data

| PCA input data | ANN input data |
| --- | --- |
| There are symptoms and root cause parameters. All the parameters are comprised in the input data. | Symptom parameters are at output. Root cause parameters are in input. |
| As PCA is capable to reduce a multivariable data sets to fewer principal component data set, many parameters in and around reactors are taken as input parameters. The scope is big enough to cover a large number of parameters to detect any abnormal event. | Only those parameters which can affect the output parameters are chosen as input parameters. All other parameters are neglected. |
| Reactor performance parameters like selectivity, oxygen conversion is taken as input parameters. | Reactor performance parameters like selectivity, oxygen conversion is normally taken as ANN output. |
| Both normal and abnormal zone parameters are collected. | Only normal plant data is collected to build a steady state model. |
| Some parameters are collected as input parameter which do not affect reactor performance but too high values or too low values thereof can cause safety incidents. An example is reactor inlet methane concentration, which when above 40 mole percent does not affect reactor performance but below 40% can produce flammable mixture. | Process variables which are not affecting the reactor performance in normal plant are ignored. |
| The scope of PCA also includes the detection of malfunction of transmitters, online analyzers etc. | Normally, the scope of an ANN model provides for detection of a change in internal characteristic of catalyst and EO reaction process. |

In Landells et al. (US patent 2010/0036529); a MPC model was initially built for refinery process. This model predicts some dependent values based on some independent process parameters. A residual is calculated by subtracting dependent variable values calculated by the predictive model from the actually measured dependent variables. In Landells et al., PCA is performed on the residual values of one or more dependent variables.

In contrast to that according to the present invention, PCA is performed on the raw process parameters rather than on any residuals.

The reasons for applying PCA on raw values are as follows:

EO catalyst characteristics are not static and change with time. Catalyst selectivity and activity is changing with the age of the catalyst (usually 2-3 years). The sensitivity of reaction input parameters (like chloride concentration, oxygen, ethylene concentration etc.) towards catalyst selectivity and catalyst activity may change with time. This change is more pronounced in high and medium selectivity catalysts. For example one unit of chloride change will change the catalyst selectivity differently at a different age of a catalyst life.

So the predictive model equations and/or model coefficient need to change accordingly as the catalyst characteristic changes.

So any static model, like MPC or DMC model (as used in Landells et al.), built for one time data, may not be valid or successful for the whole catalyst life. It needs to be rebuilt or retrained periodically.

In other words, any EO reactor model which is generating excellent prediction today may not produce accurate predictions 6 months from now as the catalyst characteristic changes with time. So it will generate large residuals in the future. If PCA applied on the residuals (as used in Landells et al.) then erroneously it will detect an abnormal event. In this case PCA could not distinguish whether large residuals are due to an abnormal process event or due to poor model prediction. Therefore, according to the present invention, PCA is applied on raw data rather than on residuals. It may eliminate any intermediate predictive model accuracy.

Implementation of PCA Model

Building the Model:

Initially all the input parameter data consisting of normal and abnormal zone data are collected as training data. Initially only data corresponding to normal operation of plant are fed to PCA algorithm and plotted against principal component axes. In the plot most of the data are concentrated in one area called normal zone.

Creation of PCA Plot for Training Data

In the present invention, it was found that first and second principal component may capture over 90% variation of the data. So, instead of monitoring 25 different parameters individually, only the first two principal components can be monitored to detect any abnormality. Once the score values of the first two principal components are obtained after running the PCA algorithm, the corresponding loading values are frozen. The calculation procedure to calculate scores and loadings are summarized in the appendix.

An ellipse is drawn around these data, as shown in FIG. 5a, which defines a 95% confidence interval. In other words, for a 95% confidence interval, 95% of the data points in the data set (normal data) fall within the threshold range of each of the two principal components. As depicted in FIG. 5a, co-ordinate values of all data of the normal zone fall within −7 to +6 for PC1 and −4.2 to +3.9 for PC2. A confidence interval ellipse is drawn accordingly, as shown in FIG. 5a.

Hotelling's $T^2$ Plot for the Training Data

In another embodiment of the invention, a $T^2$ value for each data point corresponding to normal zone is calculated. A $T^2$ value is often called a Hotelling's $T^2$ statistic, and defines the distance of a data point from an origin, for example, the distance of the data point from the intersection or origin of two or more principal components. A calculation procedure to calculate $T^2$ value is summarized in the appendix. In an example, again a 95% confidence limit line is drawn on a plot so that 95% of the data fall under this line. The value of a high limit line can be calculated by calculating 95 percentile of all $T^2$ values of all training data set. Comparing the $T^2$ value to a pre-determined threshold for example as defined by an elliptical confidence interval, provides an indication of whether an abnormal event has occurred or is occurring.

Residual Plot for the Training Data

In yet another embodiment of the invention, so-called Residuals are calculated for each data point. The Residuals represents the quantity of variance in the data that is not expressed by a pre-determined number of principal components. If the value increases, it indicates a change in the process compared to the model, which indicates a deviation from normal or expected behavior. Again, using the same procedure, a 95% confidence limit line is drawn on the plot so that 95% of the data fall under this line.

Creation of Abnormal Zone or Zones in PCA Plot

Figure 7:
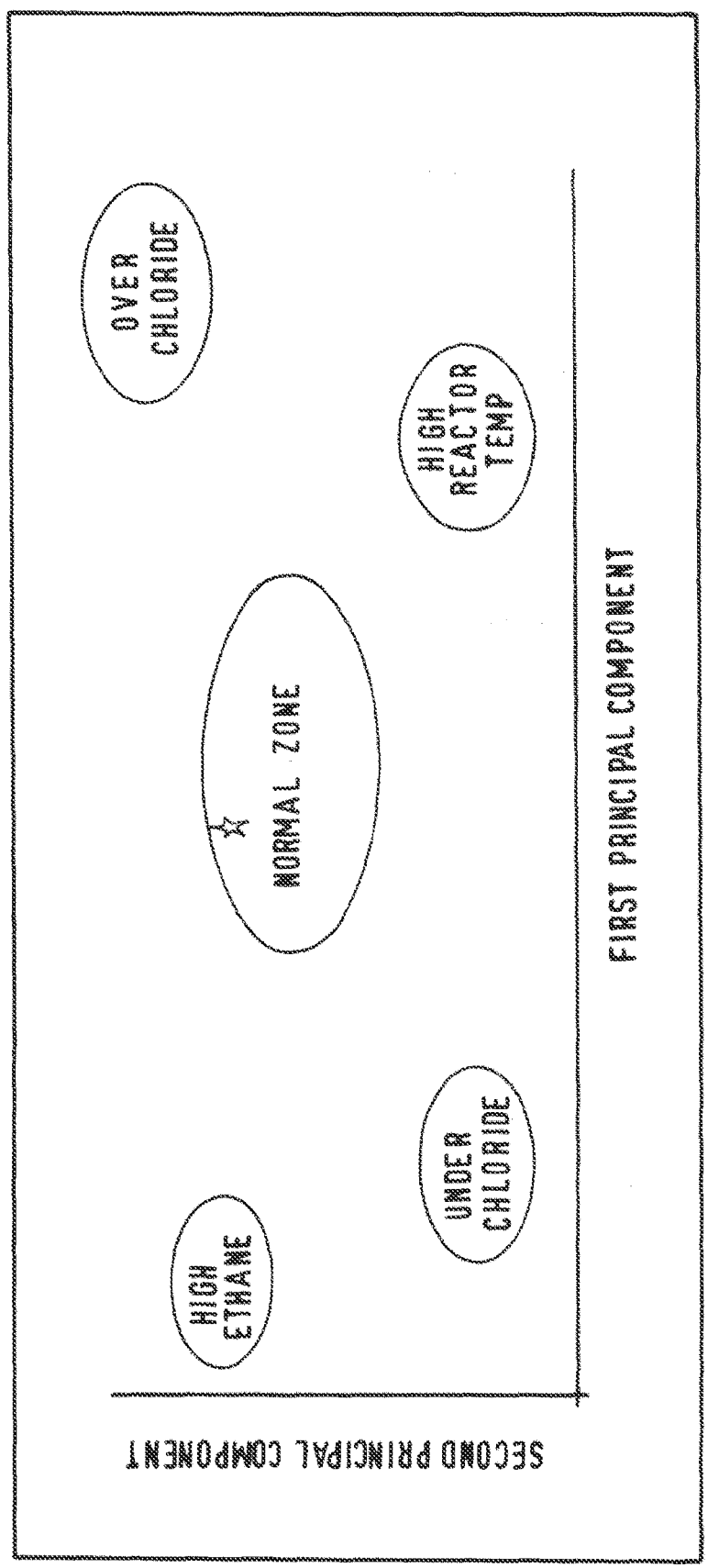
FIG. 7 shows an exemplary PCA score plot indicating a zone representative of normal plant operation and plural zones representative of abnormal plant operation.

In an example of the second part of the PCA model building, each cluster of abnormal event data is then multiplied with their corresponding loadings and scores. These score values are then plotted on the same principle component plane. These data will appear in a different concentrated zone outside an ellipse corresponding to a normal zone. Again a new ellipse is drawn on the same graph which represents a 95% confidence interval of the particular abnormal event. This ellipse is now representing the particular abnormal zone, say overchlorided zone. The same procedure is repeated for each cluster of abnormal zone data and several ellipses for each abnormal event may be drawn as a result of a model building, a picture as shown in FIG. 7 may be obtained. FIG. 7 shows a real time PCA score plot with normal zone and different abnormal zones. In this Figure, an ellipse (big center shape) may present a normal zone and all other ellipse may represent different abnormal zone, such as a zone of overchlorided phenomena, underchlorided zone, online chloride analyzer malfunction zone etc. Such a plot may identify several zones of abnormal events and the corresponding tags.

Once all the normal and abnormal areas, are drawn on the same graph, now this graph can be used to plot PCA values of real time data. Only the confidence ellipses are kept on the plot and all the training data points on the plot are removed so that this plot can be used to accommodate new real time data. For a $T^2$ plot and residual plot, only the axis and upper limit line is kept.

Fault Diagnosis Using PCA

Abnormal events can be identified from the data resulting from the PCA of the process dataset. There are a number of ways in which this may be achieved. In one embodiment of the present invention, a confidence interval is calculated based on the scores values for a pre-determined number of principal components, for example, the first two principal components. Of course more than two principal components may be applied. The confidence level can be defined based on a percentage of the data points from the data set that fall within the pre-determined confidence interval for each principal component. The pre-determined percentage of data points is typically a value in the range of 90 to 99%, for example 95% of the data points. Thus, for a 95% confidence interval, 95% of the data points in the data set fall within the threshold range for each of the two principal components. The shape of the confidence interval is typically elliptical. If the latest collected data point falls outside the confidence interval, often referred to as an outlier, then this is an indication that unusual or an abnormal event may be occurring.

In another embodiment of the invention, a $T^2$ value for each data point is calculated. A $T^2$ value is often called a Hotelling's $T^2$ statistic, and defines the distance of a data point from an origin, for example, the distance of the data point from the intersection or origin of two or more principal components. Comparing the $T^2$ value to a pre-determined threshold as defined by an elliptical confidence interval, for example, provides an indication of whether an abnormal event has or is occurring.

In yet another embodiment of the invention, so-called Residuals are calculated for each data point. Residuals represent the quantity of variance in the data that is not expressed by a pre-determined number of principal components. An increasing Residual value signifies a change in the process compared to the model, which indicates a deviation from normal or expected behavior.

The diagnostic techniques described above can be used individually or in combination in order to determine an occurrence of an abnormal event.

Implementing PCA Model in Real Time

FIG. 4: Interface between a Data historian and a dedicated PC loaded with PCA and/or ANN software, shows the data historian server (15) output interfaced with a computer (30) having principal component analysis software. The data historian server receives real time process parameters values from plant DCS or from various transmitters or sensors in plant. All data may be fed from data historian to a separate dedicated PC loaded with PCA and/or ANN software in real time. PCA scores, loadings, $T^2$ value and residual values may be calculating real time. The plots created in advance are updated with fresh real time data.

Detecting Plant is Running Normal or Abnormal in Real Time

Abnormal events may be detected manually or visually. In one embodiment, a display screen in a control room provides a user with one or more of a principal component scores plot or, a T2 plot, or a Residual plot, where an indication of the confidence interval is used to alert a user to the onset of an abnormal event. When a data point is shown to deviate outside the confidence interval, then examination of the score values and variable contributions associated therewith can be used to determine the cause of the deviation. By providing a rapid means of detecting when an abnormal event is taking place (for example from one or more of the score values of the residual PCA data, the T2 values, and the Residual), then an operator can quickly determine the causes of any deviation and assess if a manual intervention to the process is required.

Alternatively, an analysis and abnormal event detection can be performed automatically, for example, using a suitably programmed computer, which can calculate whether a data point falls outside a confidence interval on the basis of, for example, one or more of the PCA score values, the T2 values or the Residual, and identify which variables need to be altered if any, in order to rectify the cause of the abnormal event. This information can be fed as output to the process control means, which can alter one or more of the independent variables accordingly to remove the cause of the abnormal event.

Figure 5C:
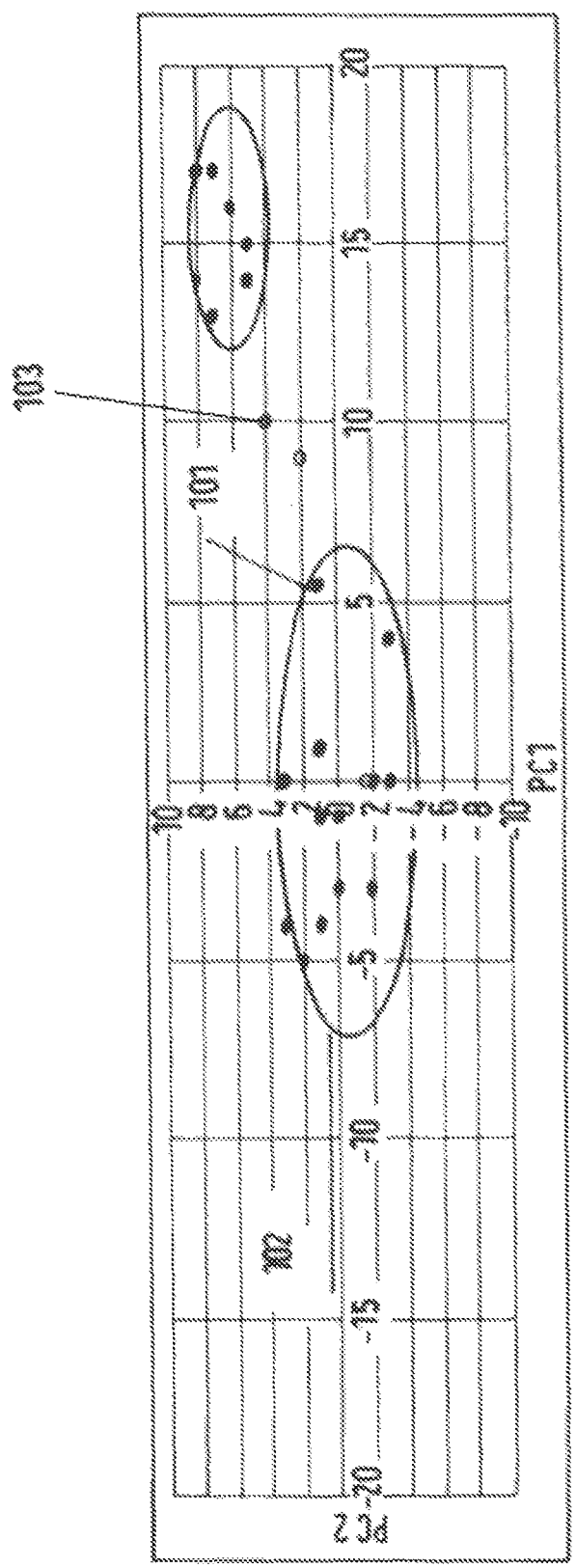
FIGS. 5b and 5c show a $T^2$ plot and a Residual plot, respectively.
Figure 5B:
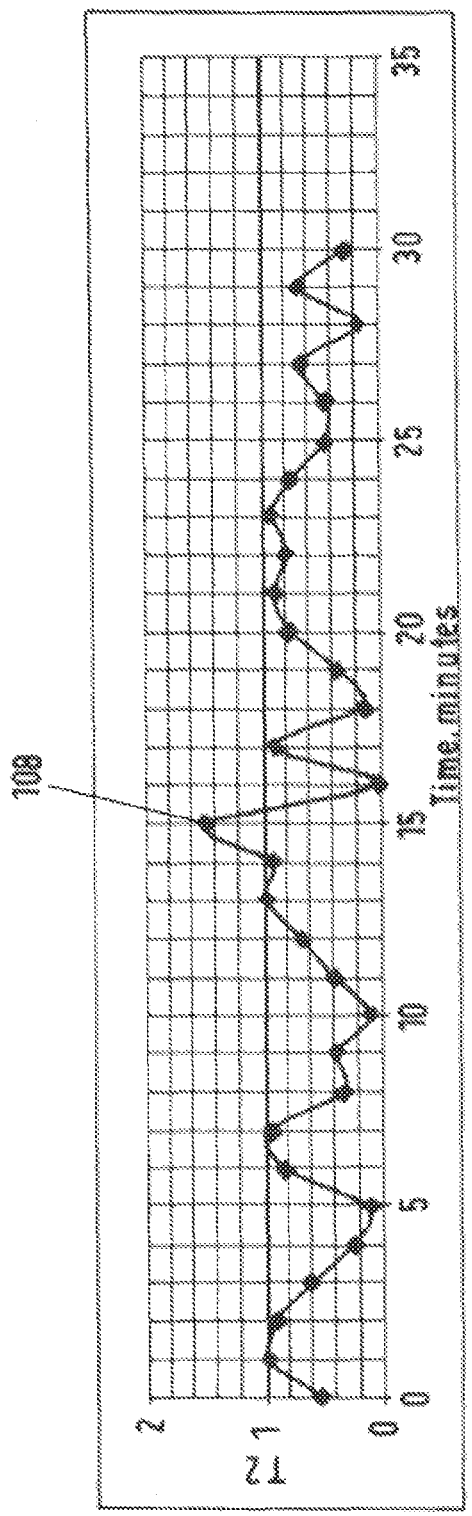
Figure 5C:
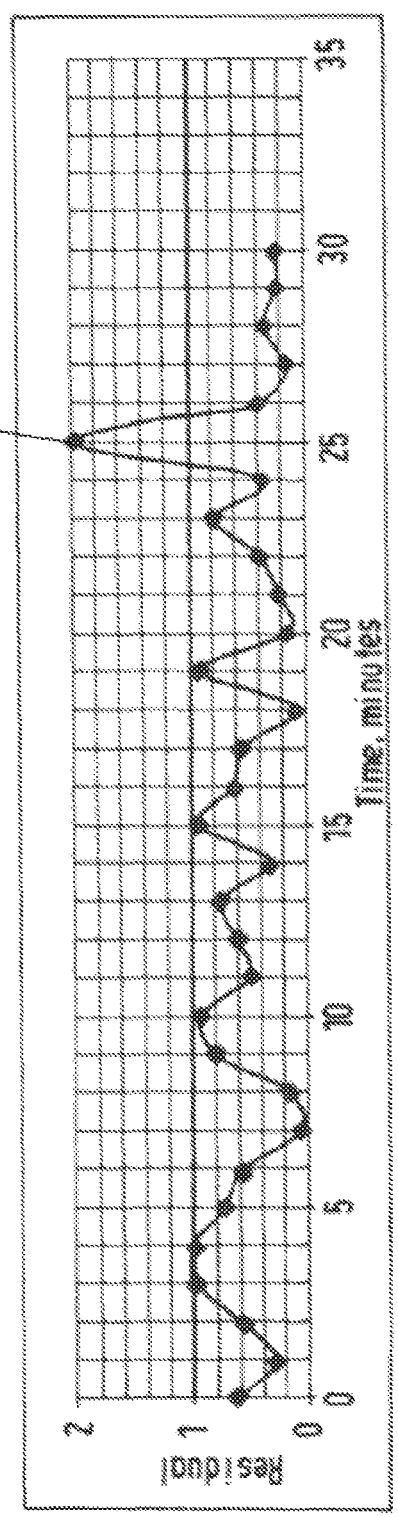

As shown in FIG. 5a-c, 5a: a PCA scores plot, 5b: a T2 plot, 5c: a Residual plot and contribution plot individually or in combination can be used to detect an abnormal event in real time. In FIG. 5a, the scores plot is a cumulative plot showing the latest data point 101 in addition to previously collected data points, plotted against the first two principal components,PC1: x axis, PC2: y axis. The position of a data point compared to a 95% confidence interval 102 provides an indication of whether a process is operating within the expected tolerances, or if an abnormal event is occurring. If an EO reaction process is running normal, the real time data point will fall inside the big ellipse designated as normal zone (refer FIG. 7). If something abnormal happened, a real time plot point will fall outside the big ellipse, i.e. the normal zone ellipse, indicating that something abnormal happened in the plant. If the real time plot point falls into any ellipse associated with an abnormal event, then user will quickly come to know which abnormal event is occurring. This provides a rapid and facile method of identifying the onset of abnormal events for which mitigating actions are already known. Corrective action may be carried out manually by an operator. Alternatively, this can be done automatically, such that recognition of an abnormal event may provide process control means with corrective action necessary to maintain optimal operation.

It may be possible that some abnormal event occurred which leads to shifting the real time plot point outside the limit of the big ellipse representing the normal zone, but it does not fall under an ellipse of any abnormal event but appears elsewhere not covered by any ellipse. This indicates that some new abnormal event may have occurred which did not occur in past i.e., which has not occurred during the period of training data. Consequently, it is possible to examine the process in detail and find out which abnormal event has occurred. The data saved in this period of time may be used to build new ellipse for new abnormal event during retraining of PCA model (described later).

Trend plots of the T2 value with time and the residual value with time are also shown in FIGS. 5b and 5c. If a process upset or other abnormal event occurs, this may be indicated by one or more increased T2 values and a score value falling outside the pre-defined 95% confidence interval 102 (FIG. 5a), as indicated for example by data point 103, which also corresponds to an increased T2 value 108, and an increase in residual value for a subsequent data point 109.

Figure 6:
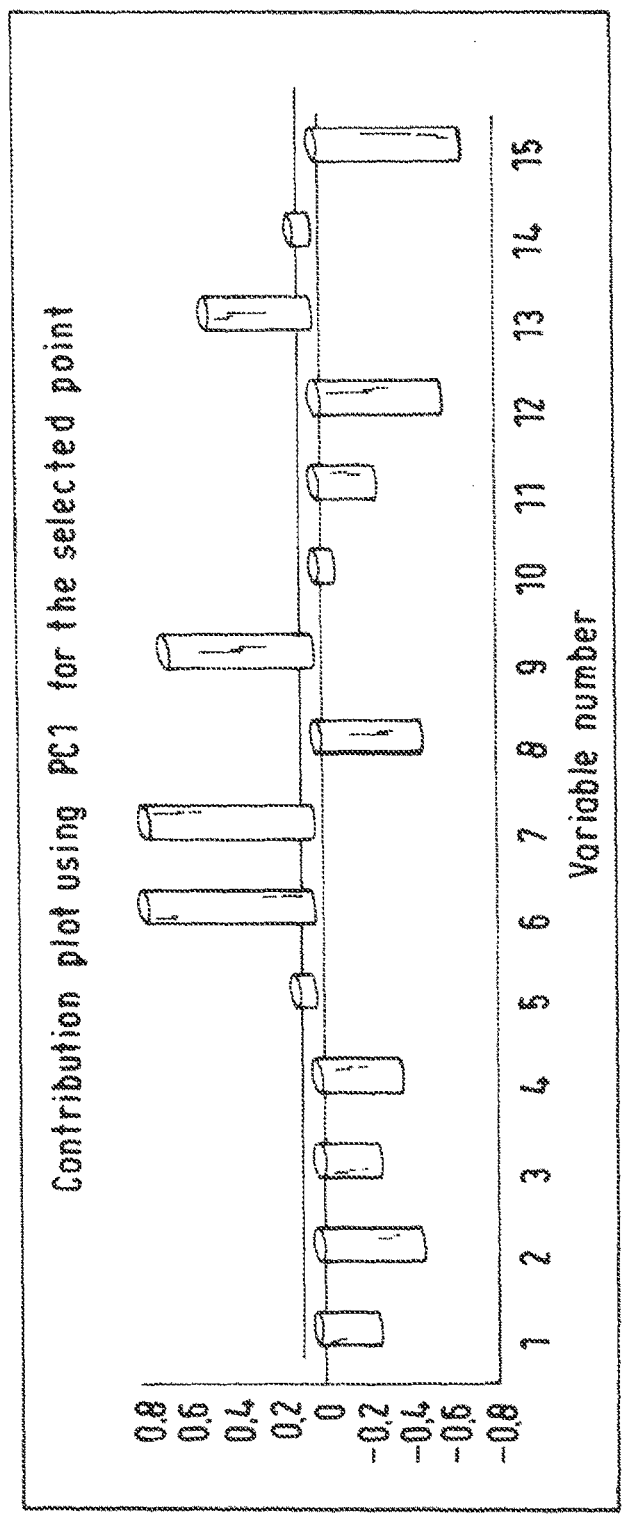
FIG. 6 plots the contribution of PCA input variables against the first principal component for a selected scores data point.

When an abnormal event is detected, the outlying data point or points can be probed by a user by examining all corresponding plots. One way is to observe a PC1 contribution plot, as shown in FIG. 6, which provides information as to which variables are associated with the abnormal event. The plot in FIG. 6 shows a contribution value y-axis for each of PCA input variable against the first principal component for a scores data point falling outside the 95% confidence limit, i.e., a contribution plot using PC1 for the selected point. Variables having high values have a high influence on the position of the data point along the specified principal component. In the example shown, the position of the scores data point in relation to the first principal component is heavily influenced in particular by variables 6, 7 and 15. Variables 1 and 5 have moderate influence on the data point.

Use of PCA Plot During Corrective Action in Real Time

Figure 8A:
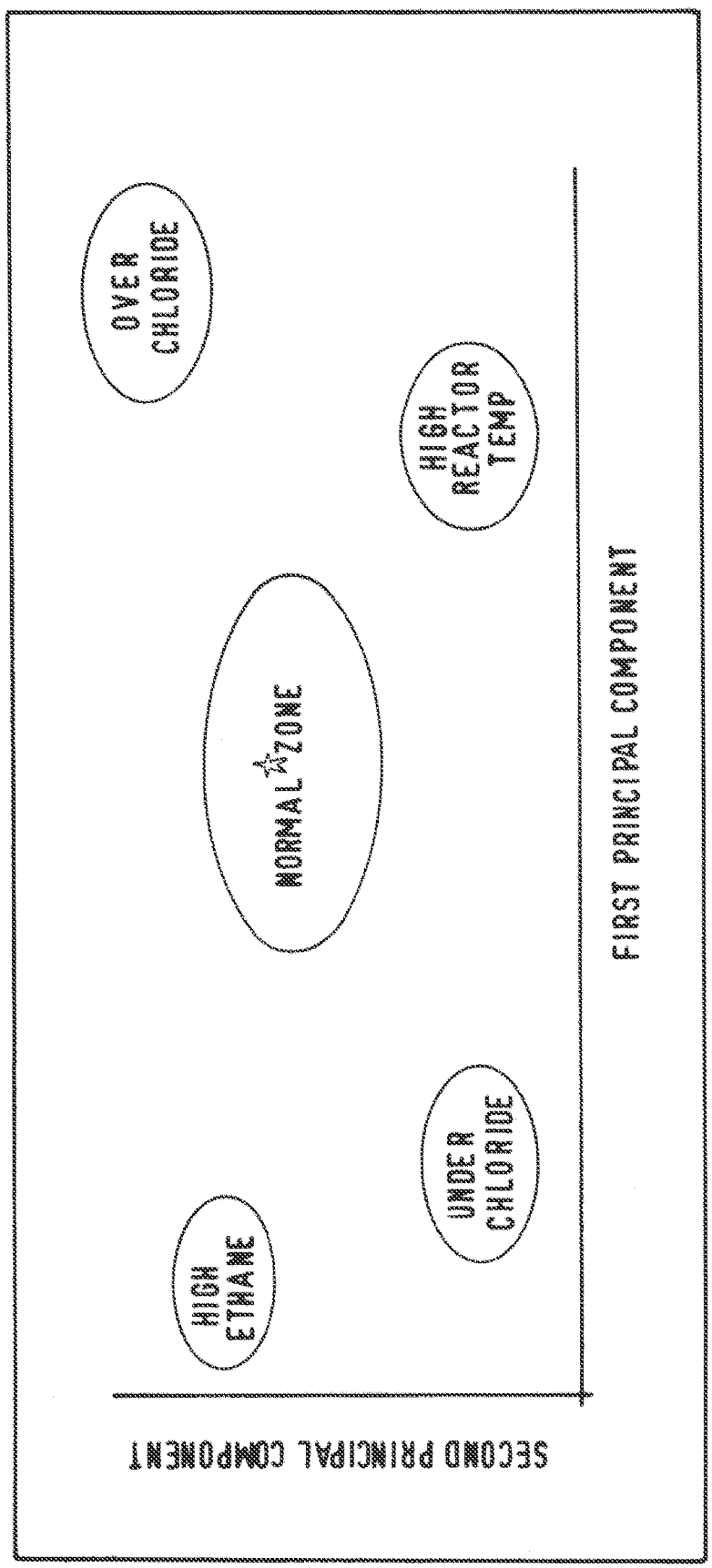
FIGS. 8a to 8f show PCA score plots indicating score points obtained under various operating conditions.
Figure 8B:
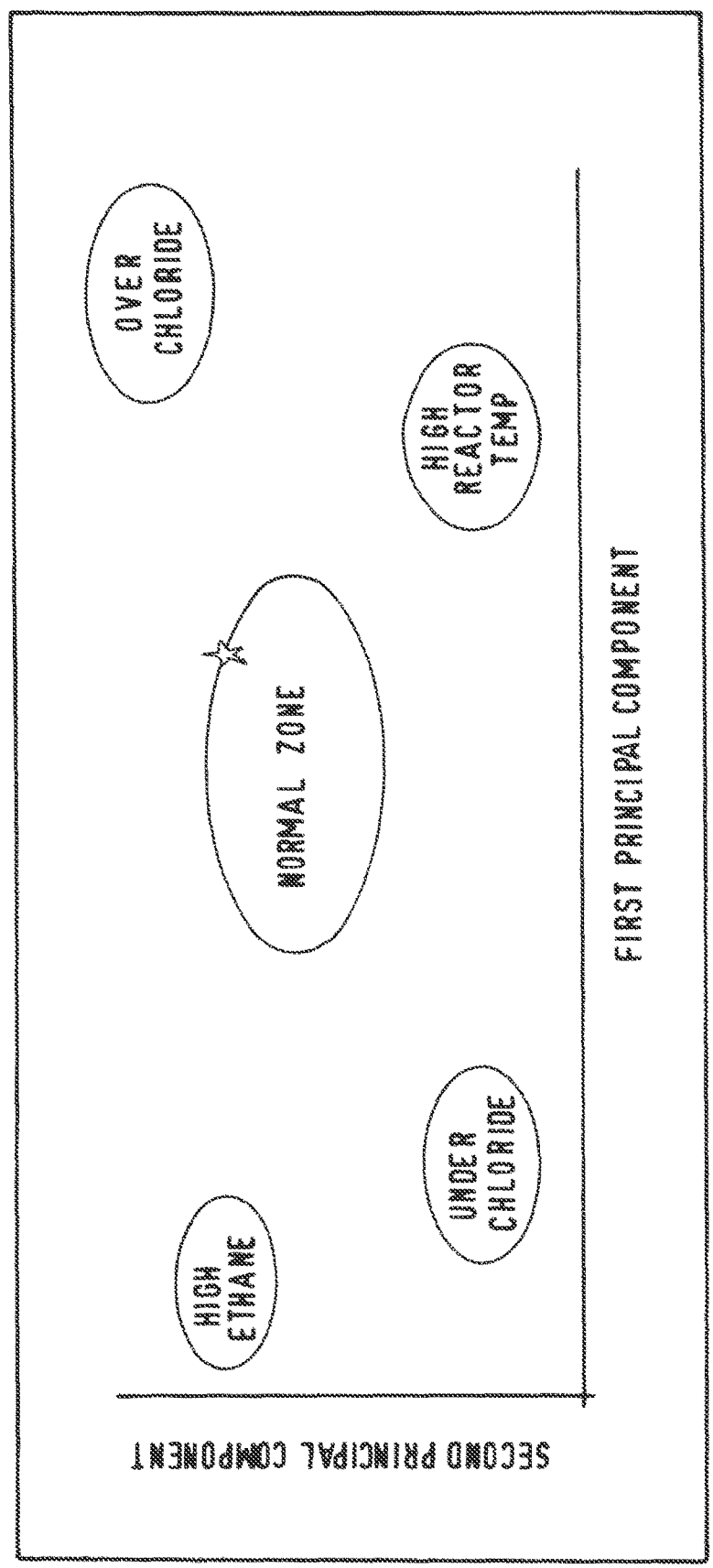
Figure 8C:
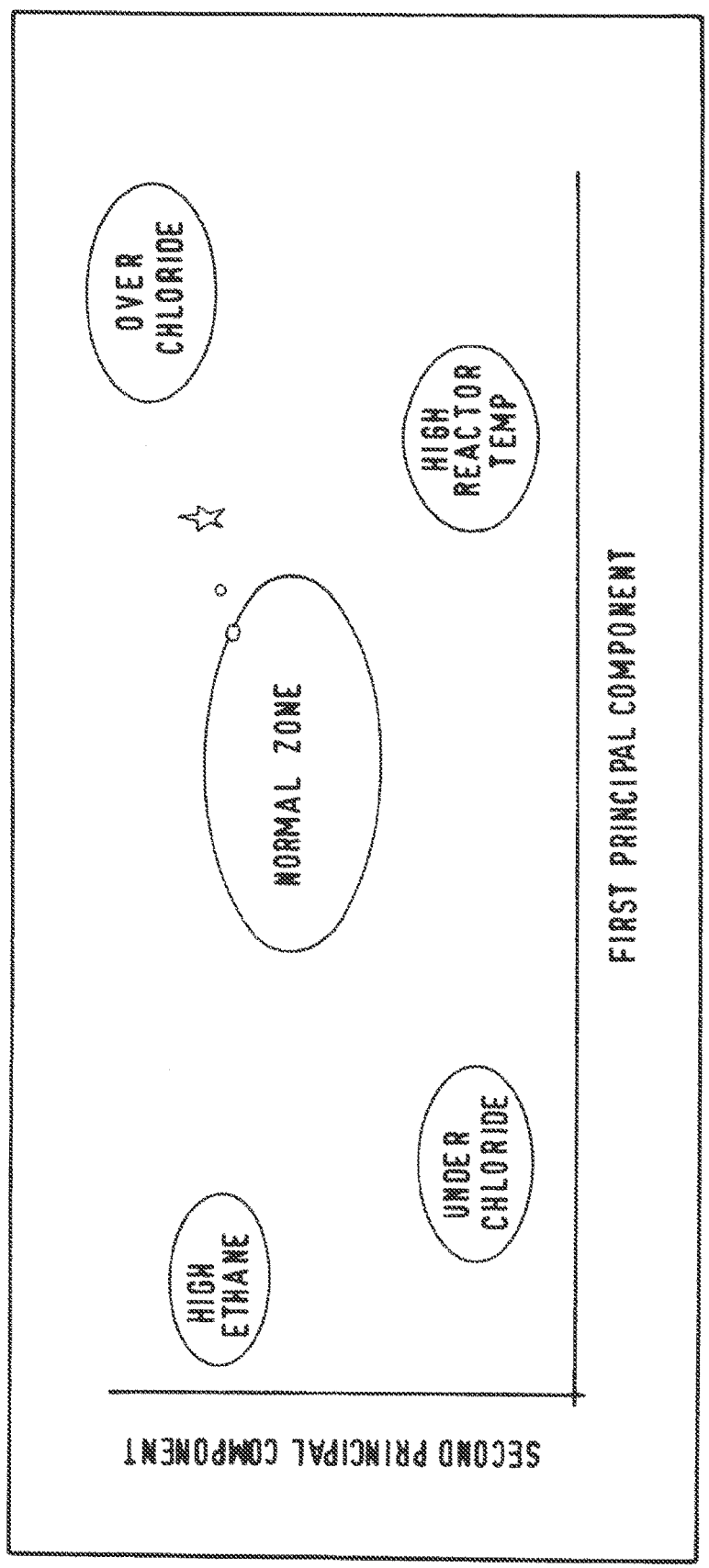
Figure 8D:
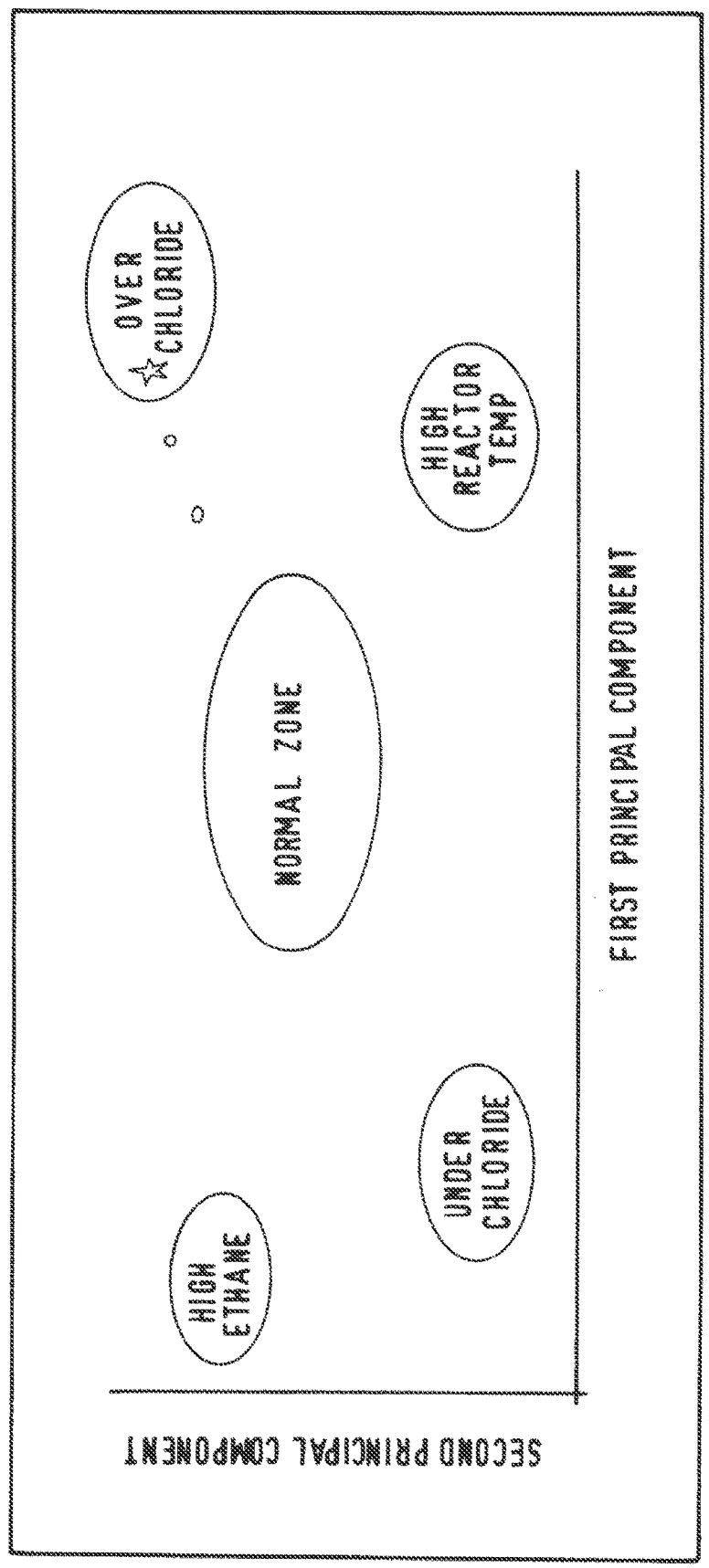
Figure 8E:
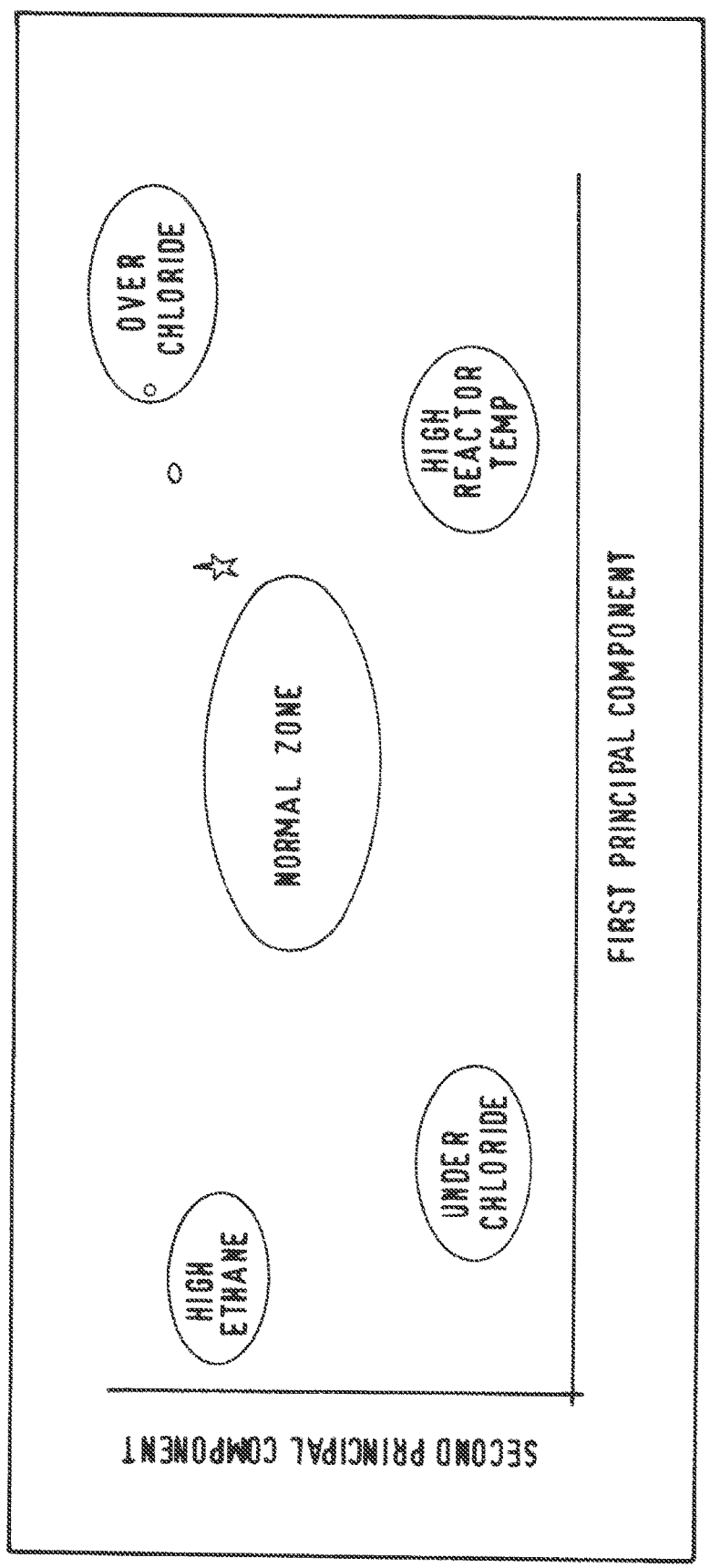
Figure 8I:
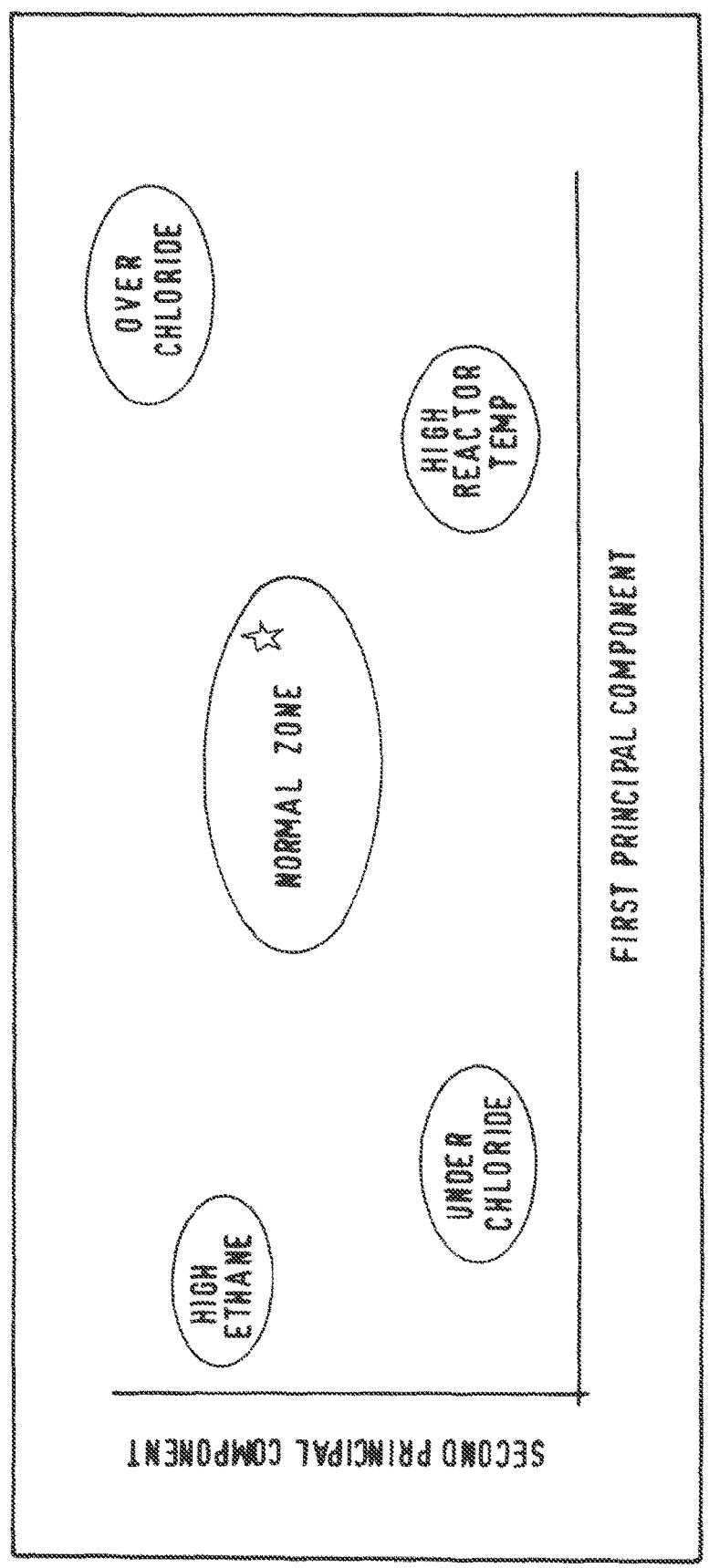

The PCA plot can be used during corrective action after abnormal event has occurred. This is explained by FIGS. 8a-8f. FIGS. 8a-8f show instances or snapshots of respective real time PCA score plots with a normal zone and different abnormal zones. Assumed that an overchlorided phenomena has occurred. FIG. 8a represents a PCA score plot during normal plant operation. As seen from FIG. 8a a real time point is well within the normal ellipse. FIG. 8b represents plant condition after 3 hours when the point representing current plant status starts moving towards the periphery of the normal ellipse. This gives early alerts to plant operator/engineers that the plant starts moving from normal to abnormal zone. FIG. 8c shows that a point is moving towards overchlorided zone ellipse. An operator can interpret this trajectory path of the point and understand that catalyst is going to be overchlorided. The operator is expected to take immediate corrective action. The operator can inspect FIG. 6, a contribution plot at that time to Figure out which is the root cause of overchlorided operation and take a corrective action to eliminate the root cause. More EDC flow may be the root cause. In case that the operator fails to take corrective action, point will shift to the over chloride ellipse and generate an alarm (FIG. 8d). It also shows the root cause in the panel as shown in FIG. 6.

Now, if an operator took a proper corrective action, the point starts moving in real time towards normal ellipse. This gives the operator an indication that the corrective action the operator has taken is correct and that the process starts moving towards normal zone, see FIG. 8e. If the operator's corrective action is not correct, the point will start moving opposite to the normal zone and diverge from the ellipse representing normal operation. If the operator's corrective action is not adequate, the point will not move and remain inside the overchloride ellipse.

In this way, the operator can understand how far the operator's corrective actions are adequate and correct. The point will move back to normal zone ellipse, see FIG. 8f after restoration of the process back to normal.

Validity of PCA Model

Time Varying Characteristic of EO Catalyst

As stated earlier, catalyst selectivity and catalyst activity is changing with the age of the catalyst. Catalyst gradually deactivate with time due to permanent loss of active sites of the catalyst due to a sintering effect. Reactor temperature and total chloride need to be increased gradually throughout the catalyst life to maintain production rate. Selectivity continually declines with time. So, a PCA model build with recent data may not be valid after 6 months. For example, reactor temperature and total chloride value which seems normal now, may not be normal after 6 months of operation. So the predictive model equations or co-efficients need to change accordingly as the catalyst characteristic changes. The PCA model needs to be retrained periodically with most recent operating data.

In order to deal with time varying characteristics of a process, quantitative criteria may be developed which can be tracked and used for retraining both the ANN and the PCA model. These include a new variable called 'Residual', which represents the goodness of the model in present conditions of process. When the value of residual is below 3, the present model can be considered good and can capture the inherent physics of the process. However, if value of residual goes beyond 3 and remains there, then it can be considered as an indication that the present ANN and/or PCA model becomes less selective and should be rebuild/retrained with recent operating data.

Capturing the Efficiency of PCA Model by Residual Plot

When an abnormal event has occurred, the following two observations can be made in the T2 plot and in the residual plot. In case the first, only the T2 value will increase above its higher limit line but the residual value will remain under its maximum limit value. This means an abnormal event has occurred but it is well accounted by the PCA model, indicated by a low residual value. The residual represents the quantity of variance in the data that is not expressed by a pre-determined number of principal components typically first 2 or 3 principal components. Normally, the residual plot will be below a threshold value represented by 95% confidence interval maximum limit line, which means most of the variation in the process data is well captured by the first two or three principal components. In the second case, when abnormal events occurred and both T2 value and residual value cross its higher limit line, this indicates that some abnormal event has occurred in the plant, which is not well represented by the present PCA model. This gives an indication to the operating people to study an event in detail. In other words, if the value of the residual increases, it indicates a characteristic change in the process as compared to the model. If this residual value suddenly goes up beyond a threshold limit and then comes back, it may be interpreted as something unexpected happened in the process which is not captured by the PCA model, i.e., it did not happen before during the period of training data. But if both the T2 and residual value remain high for a considerably long time and there is no upset or abnormality found in the process, it can be interpreted that due to catalyst behavior change, the process characteristic change permanently and its variation cannot be captured by the present model. More detailed information regarding which parameters are driving the T2 and residual values out of range can be found from the contribution plot as shown in FIG. 6. This is the time, when PCA model need to be rebuild or retrained with new recent data.

Quantitive Decision Criteria Implemented for Retraining of EO Reactor PCA Model

In example for a reactor PCA model a higher limit of T2 and for the residual is set to 3. This means, during normal operation, 95% of the calculated T2 and residual values will be less than 3. If both T2 and residual values remain above 3 for three consecutive days and there is no visible abnormality in the EO reaction process, including no malfunction of transmitters or analyzers, this can be interpreted as permanent change of process characteristic which is no longer captured by present PCA model. This is the time, when PCA model need to be rebuild or retrained with new recent data.

Retraining of PCA Model

In an example retraining was done offline by collecting most recent data of three months and a PCA model was built again following the same procedure. The input parameters may remain the same. After retraining the PCA model, the scores and loadings values will change. The new T2 and residual values will again come below their maximum limit of 3. Also new ellipse areas may be identified for any new abnormal event in retrain phase as described earlier.

Retraining of ANN Model

Basically PCA and ANN are modeling similar EO reaction process. When PCA model becomes invalid due to changes in process characteristics, it may be expected that ANN model will also become invalid. Normally, it is desirable to retrain the ANN model also when the PCA model is retrieved. This is also indicated by error percentage criteria of the ANN model. If the error percentage of the ANN model remains high above 3% for 3 consecutive days and the plant is running normal then ANN model may also be retrained. Retraining may be done offline by collecting most recent data of three months and build the ANN model again following the same procedure as described above.

Data Flow of ANN and PCA Based Fault Diagnosis

Figure 10:
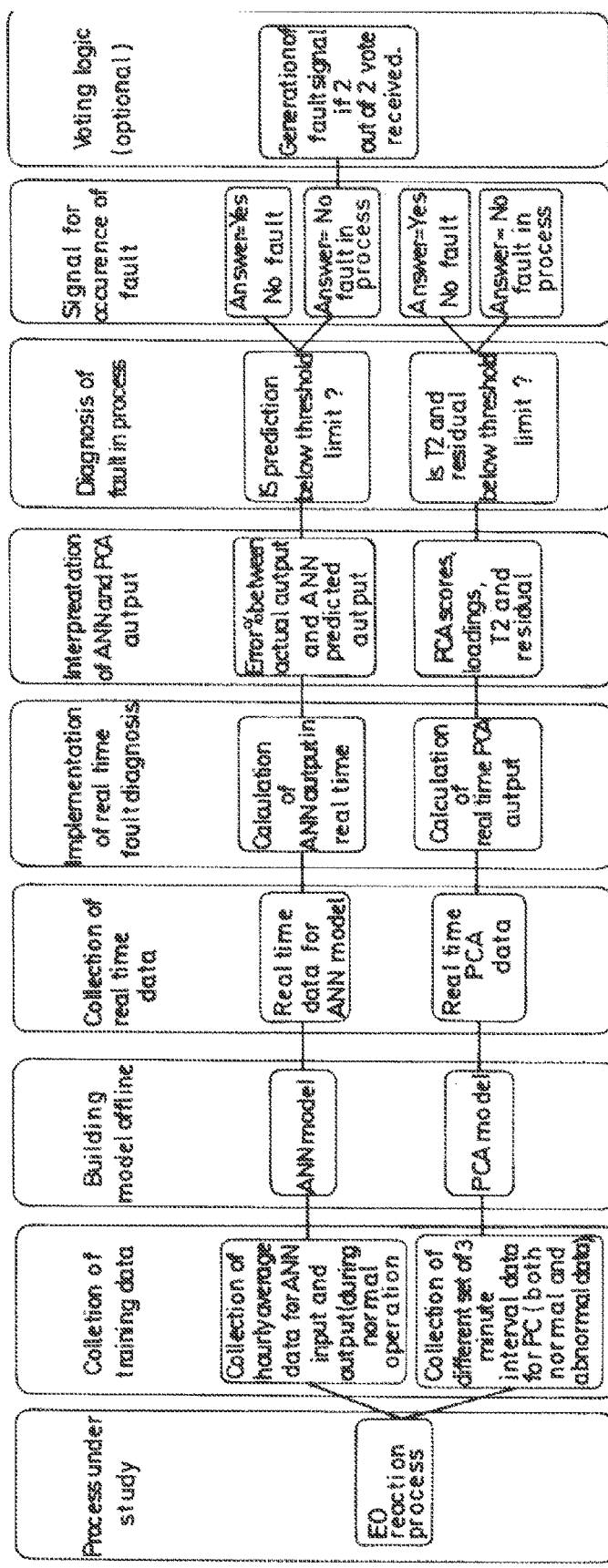
FIG. 10 schematically depicts the architecture of an ANN and PCA fault diagnostic system according to the invention.

FIG. 10: Schematic of ANN and PCA based fault diagnostic system, represents a schematic diagram of ANN and PCA based fault diagnosis. As shown in FIG. 10, both ANN and PCA based fault diagnosis systems aim to detect any fault in EO reaction process separately and independently.

Alternative approach to diagnosing a fault: ANN may try to predict the EO reaction performance parameters from the selected input parameters using the ANN model and compare the actual output with the calculated output. This is a model based approach.

On the other hand, PCA may take completely different set of inputs and convert the multi-dimensional data set to a two dimensional data set indicated by the $1^{st}$ and $2^{nd}$ principal component for easy viewing and understanding.

Different input parameters: In an example an ANN offline model was built from hourly average data for its inputs and outputs. These data were taken when plant is in normal and steady state. On the other hand, PCA data were taken as 2 minute snapshot data for different variables. PCA input parameters are considered to be more exhaustive than ANN input parameters. Also PCA input data were taken during normal and abnormal operation of plants. All the abnormal events occurred in EO reaction system in past were traced back from daily log book entries and data during that period was collected separately.

Offline Model building and online implementation: The ANN model was build offline with training data. To diagnosis a fault, the ANN model predicted output is compared with output on real time basis with error percentage between these two is above 3% generating a signal of fault. On the other hand, a PCA model generates different ellipse in principal component plane for normal operation and different abnormal operation. A point is plotted in real time in the PCA plane. The location of this point may represent the status of the plant at that moment. If this point is located inside normal ellipse, then plant is normal running. This may also be indicated by real time T2 and residual value, which will be below 3 for normal operation. On the contrary, if the point falls inside some designated ellipse representing abnormal operation, a fault signal may be generated. This is also indicated by T2 value above 3.

Independent diagnosis: ANN and PCA can be considered as two independent audits of the same process they diagnose a fault independently based on completely different sets of inputs. Their approach is different and they complement each other and can be considered redundant. The purpose of employing two different systems is to increase the reliability of detection of fault. It is known from various sources pertaining to fault diagnosis that sometimes fault diagnosis system generated fault signal even when process is normal. It confuses the users of fault diagnosis system and if erroneous detection continues over time the reliability of such system is reduced in the mind of user. To avoid that, it is proposed to implement two redundant, completely separate fault diagnosis systems. An optional voting logic can be provided for this purpose as shown in FIG. 10 to alert user for fault.

APPENDIX

Calculation of principal components
Select input variables $x_i$ based on criteria described above
Normalize $x_n = (x - x_{mean})/\sigma$ Calculate all Eigenvectors and Eigenvalues of covariance matrix $x_n^T \cdot x_n$ Arrange the Eigenvectors in order of decreasing eigenvalue. The resulting matrix is called loading matrix. First and second Eigenvector is denoted $f_1(j)$ and $f_2(j)$, respectively.

Calculate first and second principal component as $$PC1 = \sum_{i=1}^{m} x_n(j) f_1(j)$$

$$PC2 = \sum_{j=1}^{m} x_n(j) f_2(j) \qquad \text{lling's } T^2$$

Hotelling's $T^2$ calculated as follows $$T^2 = (PC_1^2/\text{Eigenvalue1}) + (PC_2^2/\text{Eigenvalue2})$$

The $T^2$ statistic gives a measure of the distance of a sample from the process mean within the plane defined by PC1 and PC2

A high $T^2$ statistic thus indicates that a sample is exhibiting an extreme variation, but well-accounted for by the PCA model.

Calculation of Residuals $$\text{Resi}(j) = x_n(j) - [(PC_1 * f_1(j)) + (PC_2 * f_2(j))]$$

$$\text{Residual} = [\Sigma \text{resi}(j)^2 / (n-2)]^{0.5}$$

Residuals give a measure of the distance of a sample perpendicular to the PC1-PC2-plane.

A high residual indicates that the sample is exhibiting a form of variation which is not well-accounted for by the PCA model.

REFERENCES

Bulsari A. B. (1994), Applications of artificial neural networks in process engineering, J. Syst. Engg. 4, 131-170

Hecht-Nielsen R. (1989), Theory of the back propagation neural network, Proceedings of the international joint conference on neural networks, 1, 593-611

Huang K., Zhan X-L, Chen F-Q, Lü D-W (2003), Catalyst design for methane oxidative coupling by using artificial neural network and hybrid genetic algorithm, Chem. Engg. Sci., 58

Lahiri S. K and Ghanta K. C (2008), Development of an artificial neural network correlation for prediction of hold-up of slurry transport in pipelines, Chemical Engineering Science 63, 1497-1509 Lahiri, S. K and Khalfe N. (2010), Modeling of commercial ethylene oxide reactor: A hybrid approach by artificial neural network & differential evolution, International J. of Chemical reactor engineering, Vol. 8, Article A4.

Riedmiller M., Braun H. (1993), A direct adaptive method for faster backpropagation learning: the RPROP algorithm, Proc. of the IEEE Int. Conf. On Neural Networks, San Francisco Calif., March 28-April 1

Gill, P. R.; Murray, W.; and Wright, M. H. (1981) "The Levenberg-Marquardt Method." §4.7.3 in Practical Optimization. London: Academic Press, pp. 136-137

Stephanopoulos G., Han C. (1996), Intelligent systems in process engineering: A review, Comp. & Chem. Engg., 20, 743-791

Tambe S. S., Kulkarni B. D., Deshpande P. B. (1996), Elements of Artificial Neural Networks with selected applications in Chemical Engineering and Chemical & Biological Sciences, Simulations & Advanced Controls, Louisville, Ky.

What we claim is:

1. A system for monitoring a process determined by a set of process data in a multidimensional process data domain pertaining to process input-output data, the system comprising:
    means for acquiring a plurality of historic process data sets;
    means for obtaining a transformation from the multidimensional process data domain to a model data domain of lower dimension by performing multivariate data analysis;
    means for transforming a current process data set to a model data set to monitor the process using the obtained transformation; and
    means to detect a permanent change of a process characteristic of the process which is no longer captured by the multivariate data analysis based on observing Residuals exceeding a predetermined threshold for a predetermined amount of time.

2. The system according to claim 1, wherein said performing multivariate data analysis comprises principal component analysis.

3. The system according to claim 1, wherein said performing multivariate data analysis comprises establishing an artificial neural network.

4. The system according to claim 1, further comprising:
    means for designating one or more portions of the model data domain, each portion holding model data sets representative of a normal operating condition or a specific abnormal operating condition of the process based on one or more clusters of model data sets obtainable from historic process data sets collected during normal events and collected separately during abnormal events; and
    means for diagnosing for a current model data set an operating condition of the process by identifying one of the one or more designated portions of the model data domain which holds the current model data set.

5. The system according to claim 4, wherein diagnosing an operating condition of the process for the current model data set comprises fault diagnosing indicative of one or more abnormal operating conditions.

6. The system according to claim 5, wherein fault diagnosing comprises diagnosing overchloridization or underchloridization of a catalyst as abnormal operating conditions by identifying the one of the one or more designated portions of the model data domain which holds the current model data set that corresponds to the overchloridization or underchloridization abnormal operating conditions.

7. The system according to claim 4, wherein diagnosing an operating condition of the process for the current model data set comprises determining a Residual indicative of a quantity of variance in the current model data set.

8. The system according to claim 1, wherein the process is a chemical process.

9. The system according to claim 8, wherein the chemical process comprises oxidation of ethylene to produce ethylene oxide in a reactor system.

10. The system according to claim 9, wherein the process input-output data represented by the process data domain are selected from the group of the following parameters measured at the reactor system used for ethylene oxide production:
    input parameters: Reactor $O_2$ inlet concentration, $C_2H_4$ inlet concentration, $CO_2$ inlet concentration, gas hourly space velocity, delta EO across reactor, work rate, cumulative EO production, total chloride concentration, scrubber top temperature and wash tower top temperature;

output parameters: oxygen conversion, feed selectivity and reactor coolant temperature.

11. The system according to claim 1, wherein current process data are obtained in real time and/or operating conditions are diagnosed in real time.

12. A method for monitoring a process determined by a set of process data in a multidimensional process data domain representing process input-output data, the method comprising:

acquiring a plurality of historic process data sets;

obtaining a transformation from the multidimensional process data domain to a model data domain of lower dimension by performing multivariate data analysis;

transforming a current process data set to a model data set to monitor the process using the obtained transformation; and detecting a permanent change of a process characteristic of the process which is no longer captured by the multivariate data analysis based on observing Residuals exceeding a predetermined threshold for a predetermined amount of time.

13. The method according to claim 12, wherein performing multivariate data analysis comprises principal component analysis.

14. The method according to claim 12, wherein performing multivariate data analysis comprises establishing an artificial neural network.

15. The method according to claim 12, further comprising:

designating one or more portions of the model data domain, each portion holding model data sets representative of a normal operating condition or a specific abnormal operating condition of the process based on or more clusters of model data sets obtainable from historic process data sets collected during normal events and collected separately during abnormal events; and diagnosing for a current model data set an operating condition of the process by identifying one of the one or more designated portions of the model data domain which holds the current model data set.

16. The method according to claim 15, wherein diagnosing an operating condition of the process for a current model data set comprises fault diagnosing indicative of one or more abnormal operating conditions.

17. The method according to claim 16, wherein fault diagnosing comprises diagnosing overchloridization or underchloridization of a catalyst as abnormal operating conditions by identifying the one of the one or more designated portions of the model data domain which holds the current model data set that corresponds to the overchloridization or underchloridization abnormal operating conditions.

18. The method according to claim 15, wherein diagnosing an operating condition of the process for the current model data set comprises fault diagnosing indicative of one or more abnormal operating conditions.

19. The method according to claim 12, wherein diagnosing an operating condition of the process for the current model data set comprises determining a Residual indicative of a quantity of variance in the current model data set.

20. The method according to claim 12, wherein the process is a chemical process.

21. The method according to claim 20, wherein the chemical process comprises oxidation of ethylene to produce ethylene oxide in a reactor system.

22. The method according to claim 21, wherein the process input-output data represented by the process data domain are selected from the group of the following parameters measured at the reactor system used for ethylene oxide production:

input parameters: Reactor $O_2$ inlet concentration, $C_2H_4$ inlet concentration, $CO_2$ inlet concentration, gas hourly space velocity, delta EO across reactor, work rate, cumulative EO production, total chloride concentration, scrubber top temperature and wash tower top temperature;

output parameters: oxygen conversion, feed selectivity and reactor coolant temperature.

23. The method according to claim 12, wherein current process data are obtained in real time and/or operating conditions are diagnosed in real time.

24. A computer program product comprising a non-transitory computer-readable medium embodying program instructions for causing a system to perform the steps of:

acquiring a plurality of historic process data sets;

obtaining a transformation from the multidimensional process data domain to a model data domain of lower dimension by performing multivariate data analysis;

transforming a current process data set to a model data set to monitor the process using the obtained transformation; and detecting a permanent change of a process characteristic of the process which is no longer captured by the multivariate data analysis based on observing Residuals exceeding a predetermined threshold for a predetermined amount of time.

* * * * *